(12) United States Patent
Shetty et al.

(10) Patent No.: US 10,365,405 B2
(45) Date of Patent: Jul. 30, 2019

(54) METHOD FOR DETERMINING FORMATION PROPERTIES BY INVERSION OF MULTISENSOR WELLBORE LOGGING DATA

(71) Applicant: SCHLUMBERGER TECHNOLOGY CORPORATION, Sugar Land, TX (US)

(72) Inventors: Sushil Shetty, Arlington, MA (US); Lin Liang, Belmont, MA (US); Tarek M. Habashy, Burlington, MA (US); Vanessa Simoes, Sao Paulo (BR); Austin Boyd, Ridgefield, CT (US); Bikash K. Sinha, Cambridge, MA (US); Smaine Zeroug, Lexington, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/544,187

(22) PCT Filed: Jan. 25, 2016

(86) PCT No.: PCT/US2016/014710
§ 371 (c)(1),
(2) Date: Jul. 17, 2017

(87) PCT Pub. No.: WO2016/123014
PCT Pub. Date: Aug. 4, 2016

(65) Prior Publication Data
US 2017/0371072 A1 Dec. 28, 2017

Related U.S. Application Data

(60) Provisional application No. 62/107,574, filed on Jan. 26, 2015, provisional application No. 62/171,033, filed on Jun. 4, 2015.

(51) Int. Cl.
*G01V 99/00* (2009.01)
*G01V 11/00* (2006.01)
*G01N 15/08* (2006.01)

(52) U.S. Cl.
CPC ........ *G01V 99/005* (2013.01); *G01N 15/088* (2013.01); *G01V 11/00* (2013.01); *G01V 2210/1429* (2013.01); *G01V 2210/622* (2013.01)

(58) Field of Classification Search
CPC .................................................... G01V 99/005
(Continued)

(56) References Cited

U.S. PATENT DOCUMENTS

2004/0244972 A1 * 12/2004 Sayers .................. E21B 21/08
166/250.15
2005/0242807 A1   11/2005 Freedman
(Continued)

FOREIGN PATENT DOCUMENTS

WO  WO 2007/001746  *  1/2007
WO  2010083388 A2   7/2010
WO  2014025354 A1   2/2014

OTHER PUBLICATIONS

Braunisch, et al, "Inversion of Guided-Wave Dispersion Data with Application to Borehole Acoustics", J. Acoust. Soc. Am. 115 (1), Jan. 2004, pp. 269-279.
(Continued)

*Primary Examiner* — Hien D Khuu

(57) ABSTRACT

A computer-implemented method is provided for determining properties of a formation traversed by a well or wellbore. A formation model describing formation properties at an interval-of-interest within the well or wellbore is derived from measured sonic data, resistivity data, and density data for the interval-of-interest. The formation model is used as input to a plurality of petrophysical transforms and corresponding tool response simulators that derive simulated sonic data, resistivity data, and density data for the interval-of-interest. The measured sonic data, resistivity data, and density data for the interval-of-interest and the simulated sonic data, resistivity data, and density data for the interval-of-interest are used by an inversion process to refine the
(Continued)

formation model and determine properties of the formation at the interval-of-interest. In embodiments, properties of the formation may be radial profiles for porosity, water saturation, gas or oil saturation, or pore aspect ratio.

23 Claims, 21 Drawing Sheets

(58) Field of Classification Search
USPC .............................................................. 702/7
See application file for complete search history.

(56) References Cited

U.S. PATENT DOCUMENTS

| 2008/0065362 | A1 | 3/2008 | Lee et al. | |
| 2009/0145600 | A1* | 6/2009 | Wu | G01V 1/50 |
| | | | | 166/250.02 |
| 2009/0260880 | A1* | 10/2009 | Thambynayagam | E21B 43/00 |
| | | | | 175/45 |
| 2010/0286967 | A1 | 11/2010 | Vasilevskiy et al. | |
| 2016/0130916 | A1* | 5/2016 | Abadie | G01V 99/005 |
| | | | | 703/10 |

OTHER PUBLICATIONS

Burridge, et al., "Inversion for Formation Shear Modulus and Radial Depth of Investigation Using Borehole Flexural Waves," SEG Annual Meeting, (Nov. 10-15, 1996) 4 pages.

Gao, et al., "Borehole Petrophysical Imaging Using Induction and Acoustic Measurements", Petrophysics, vol. 54 (4) Aug. 2013, pp. 383-394.

Habashy, et al., "A General Framework for Constraint Minimization for the Inversion of Electromagnetic Measurements", PIER, 46 (2004) pp. 265-312.

Howard, "A New Invasion Model for Resistivity Log Interpretation", The Log Analysist 33 (02) pp. 96-110.

Mallan, et al., "Joint Radial Inversion of Resistivity and Sonic Logs to Estimate In-Situ Petrophysical and Elastic Properties of Formations", SPE 124624, (2009) 8 pages.

Mavko, et al., "The Rock Physics Handbook, Second Edition—Tools for Seismic Analysis of Pourous Media", (2009) Cambridge University Press, 13 pages.

Pistre, et al., "A Modular Wireline Sonic Tool for Measurements of 3D (Azimuthal, Radial, and Axial) Formation Acoustic Properties", SPWLA 46th, Annual Logging Symposium, Jun. 26-29, 2005, 13 pages.

Rosthal, et al. "Field Test Results of an Experimental Fully-Triaxial Induction Tool", SPWLA 44th Annual Logging Symposium, Jun. 22-25, 2003, 14 pages.

Shetty, et al, "Inversion-Based Method Integrating Sonic and Resistivity Logging Data for Estimation of Radial Water Saturation and Porosity Near the Wellbore", SPE-170609-MS, Oct. 27-29, 2014, 10 pages.

Xu, et al., "A New Velocity Model for Clay-Sand Mixtures", Geophysical Prospecting (1995), vol. 43, pp. 91-118.

Zeroug, et al., "Monopole Radial Profiling of Compressional Slowness", SEG Annual Meeting (2006), pp. 354-358.

\* cited by examiner

METHOD FOR DETERMINING FORMATION PROPERTIES BY INVERSION OF MULTISENSOR WELLBORE LOGGING DATA

RELATED APPLICATIONS

The present application claims the benefit of Provisional Application Ser. No. 62/107,574, filed on Jan. 26, 2015 and entitled "METHOD FOR DETERMINING FORMATION PROPERTIES BY INVERTING WELL LOGGING DATA," and Provisional Application Ser. No. 62/171,033, filed on Jun. 4, 2015 and entitled "METHOD FOR DETERMINING FORMATION PROPERTIES BY INVERTING WELL LOGGING DATA," which are hereby incorporated by reference in their entireties.

FIELD

This disclosure relates to well logging in oil and gas fields. In particular, this disclosure relates to determining reservoir formation properties using well log data.

BACKGROUND

Accurate estimation of formation properties requires that the interpretation of the well log data account for the effects of drilling-induced near-wellbore alteration caused by mud-filtrate invasion or mechanical damage. Currently, this is achieved through inversion of resistivity log data to provide a radial profile of resistivity near the wellbore, a separate inversion of density logging data to provide a radially constant density near the wellbore, and a separate inversion of sonic log data to provide a radial profile of shear wave velocity and compressional wave velocity near the wellbore. However, water saturation and porosity derived from these inversions may not be mutually consistent because of different formation volumes probed by the various log data, restrictive formation models, or nonuniqueness of the inversion solution. This has led to the development of multiphysics inversion-based methods that integrate data from several logging tools to produce robust and accurate interpretations consistent with all the data. However, these inversion-based methods integrate only sonic data and resistivity data.

SUMMARY

The formation model and inversion workflow described herein can facilitate estimating porosity and water saturation in situations where the pore fluid consists of three fluid phases, e.g., gas, water and oil. This situation can occur in gas-bearing formations drilled with oil-based mud by invasion of the oil phase from the mud filtrate into the pores. Resistivity data cannot distinguish between oil and gas, and sonic data corresponding to the shear wave velocity has very weak sensitivity to the pore fluid. Therefore these data are not useful for characterizing relative proportion of gas and oil. In contrast, density data and sonic data corresponding to the compressional wave velocity are more sensitive to proportion of gas in the formation. This fact can be utilized to build a joint inversion framework for estimating pore aspect ratio, porosity, water saturation, oil saturation, and gas saturation from sonic data, density data, and resistivity data.

Illustrative embodiments of the present disclosure are directed to a method for determining properties of a geological formation using well log data. The method includes measuring and/or receiving sonic data, resistivity data, and density data of the geological formation for an interval-of-interest within a well or wellbore. The method further includes jointly inverting resistivity data, sonic data, and density data to determine properties of the formation at the interval-of-interest. In one embodiment, the properties of the formation can include (i) a radial profile for porosity ($\phi$) at the interval-of-interest, (ii) a radial profile for water saturation ($S_w$) at the interval-of-interest, and/or (iii) a pore aspect ratio ($\alpha$) at the interval-of-interest. In another embodiment, the properties of the formation can include (i) a porosity at the interval-if interest, (ii) a radial profile of water saturation at the interval of interest, (iii) a radial profile of gas saturation at the interval of interest, (iv) a radial profile of oil saturation at the interval of interest, and (v) a radial profile of pore aspect ratio at the interval-of-interest.

In one embodiment, the formation properties are parameterized by a formation model derived from a joint-inversion process that uses petrophysical transforms and tool response simulators to derive simulated log data at the interval-of-interest, where the simulated log data includes simulated resistivity data, sonic data, and density data. The simulated log data for the interval-of-interest is compared to measured log data for the interval-of-interest in order to refine (tune) the formation model.

For example, in one embodiment, the radial porosity profile and pore aspect ratio of the formation model can be refined based on a comparison of the simulated and measured sonic data as well as comparison of the simulated and measured density data. Also, the radial water saturation profile of the formation model can be refined based on a comparison of the simulated and measured resistivity data, while the porosity and pore aspect ratio are held fixed. In another embodiment, the radial profile of pore aspect ratio, radial profile of gas saturation, radial profile of oil saturation, and porosity can be refined based on a comparison of the simulated and measured sonic data as well as comparison of the simulated and measured density data.

BRIEF DESCRIPTION OF THE DRAWINGS

Those skilled in the art should more fully appreciate advantages of various embodiments of the present disclosure from the following "Detailed Description" discussed with reference to the drawings summarized immediately below.

DETAILED DESCRIPTION

The present disclosure is directed to an inversion-based method that integrates resistivity data, sonic data, and density data of a geological formation acquired from within a well (or wellbore) that traverses the geological formation. At each interval-of-interest within the well, properties of the geological formation are parameterized by a formation model. In one embodiment, the formation model includes (i) a radial profile of water saturation at the interval-of-interest, (ii) a radial profile of porosity at the interval-of-interest, and (ii) a pore aspect ratio at the interval-of-interest (which is assumed to be uniform and constant in the radial direction at the interval of interest). The term "radial" means in a direction that extends laterally from the center of the well (or wellbore) into the geological formation. Radial changes in water saturation represent the effect of mud-filtrate invasion, while radial changes in porosity represent the effect of mechanical alteration of the rock or fines migration. The term "interval-of-interest" means a portion of the well corresponding to a location (depth) or measurement station within the well. The formation properties are estimated from the data using a workflow that exploits complementary physical sensitivities and different radial depths of investigation (DOI) of the various measurements. Petrophysical transforms (which are specific to the formation lithology) can be used to map radial profiles of water saturation and porosity to radial profiles of elastic properties and radial profiles of electromagnetic properties. The electromagnetic properties include resistivity, while the elastic properties include compressional wave velocity, shear wave velocity, and density. The radial profiles of resistivity, compressional wave velocity, shear wave velocity, and density can be input to tool response simulators, which are used as forward models in a joint inversion process, discussed in greater detail below.

Forward Modeling

Figure 1A:
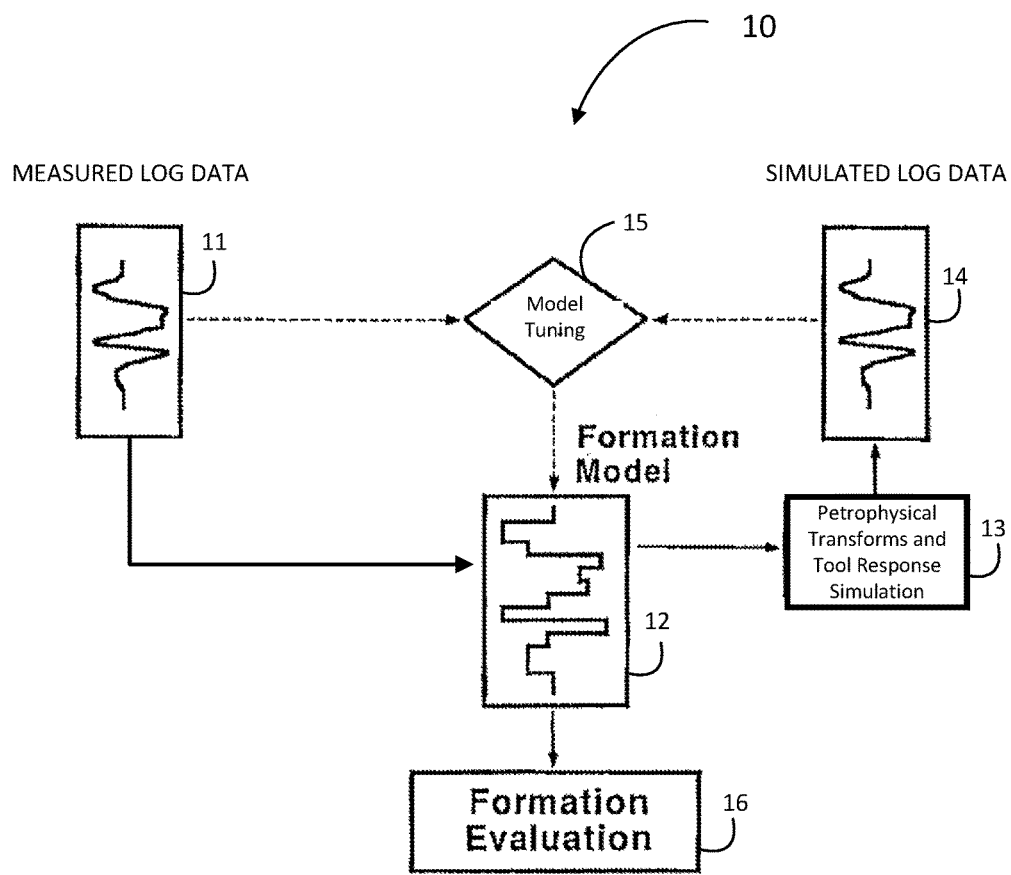
FIG. 1A shows a flowchart illustrating the use of forward modeling in a log interpretation method in accordance with one embodiment of the present disclosure.

The systematic application of forward modeling in log interpretation is illustrated in the workflow 10 in FIG. 1A. At block 11, measurements of sonic data, resistivity data, and density data (measured log data) that characterize the geological formation are obtained at an interval of interest in the well (or wellbore). The measurements at block 11 can be used to derive initial estimates of values for a formation model for the interval-of-interest (block 12). Various algorithms and simulations may be used at block 13 to process the formation model to derive simulated sonic data, simulated resistivity data, and simulated density data (simulated log data) for the interval of interest (block 14). At block 15, the simulated log data can be compared to the measured log data obtained at block 11 in order to revise the formation model for the interval-of-interest. The operations of block 13 and 15 can be repeated in an iterative manner until reasonable agreement (e.g., within a predefined threshold) is achieved between the measured log data and the simulated log data. At block 16, an evaluation of the final formation model for one or more interval-of-interests within the well (or wellbore) may be performed for reservoir analysis.

Figure 1B:
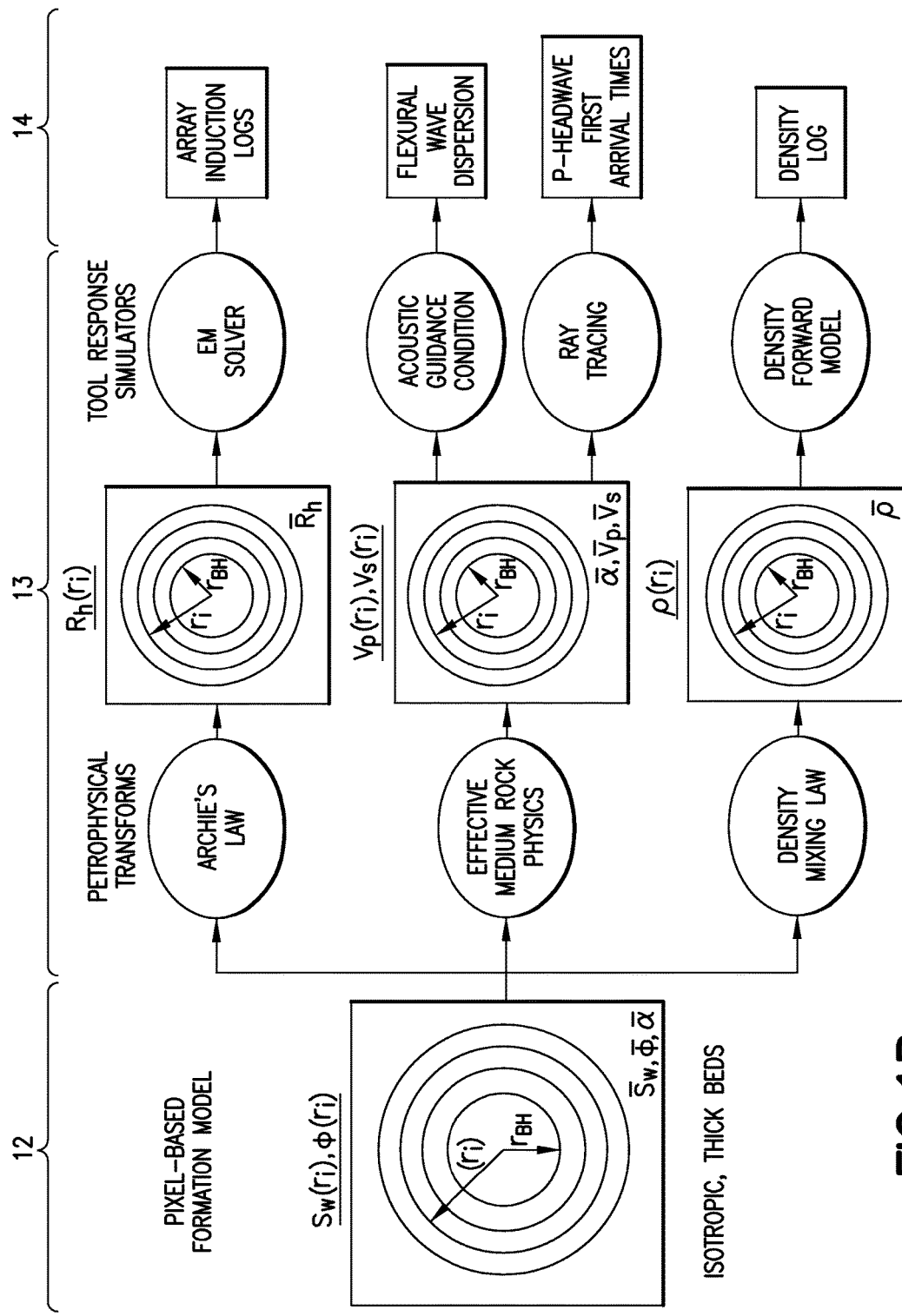
FIG. 1B shows a forward modeling method in accordance with one embodiment of the present disclosure.

FIG. 1B shows an embodiment of blocks 12, 13, and 14 of the workflow 10 of FIG. 1A in greater detail. The formation at a respective interval-of-interest may be described by a one-dimensional radial formation model with properties defined in discrete bins or pixels. Here, a one-dimensional radial formation implies that the formation properties vary only in the radial direction, but are constant in the vertical and azimuthal directions. Also, here, the term "vertical" means in a direction along the wellbore. The term "azimuthal" means in a direction around the wellbore. An example of a one-dimensional radial formation model is shown graphically in the image on the left in FIG. 1B. The formation model contains $N^{pixels}$ labelled $i=1, \ldots, N^{pixels}$. The water saturation and porosity in a pixel at radius $r_i$ are denoted by $S_w(r_i)$ and $\phi(r_i)$ respectively. The radius $r_i$ relates to radial distance from the center of the circular well (or wellbore). The well (or wellbore) extends radially to radius $r_{BH}$. An outermost pixel is unbounded in radial extent and represents the virgin, far-field formation, with water saturation $\bar{S}_w$ and porosity $\bar{\phi}$. The pore aspect ratio ($\alpha$) is modeled as being constant in each pixel. The radial variation in water saturation ($S_w$) and porosity ($\phi$) capture the effect of mud filtrate invasion and mechanical damage respectively. The geological formation is assumed to be isotropic, which implies that the elastic properties and electromagnetic properties of the formation are directionally invariant in each pixel.

Once the formation model is defined, petrophysical transforms can be employed to map the water saturation ($S_w$), porosity ($\phi$), and pore aspect ratio ($\alpha$) in each pixel of the formation model to a number of parameters that represent the radial profile of various elastic properties and electromagnetic properties of the formation at the interval-of-interest. In one embodiment, the parameters include a resistivity parameter $R_t(r_i)$ that represents the radial profile of resistivity of the formation at the interval-of-interest, a compressional velocity parameter $V_p(r_i)$ that represents the radial profile of compressional wave velocity of the formation at the interval-of-interest, a shear wave velocity parameter $V_s(r_i)$ that represents the radial profile of shear wave velocity of the formation at the interval-of-interest, and a density parameter $\rho(r_i)$ that represents the radial profile of density of the formation at the interval-of-interest. As shown in FIG. 1B, a resistivity-saturation transform (e.g., based on Archie's Law) can be used to compute the resistivity parameter $R_t(r_i)$, a rock physics transform based on a rock physics model can be used to compute the compressional wave velocity parameter $V_p(r_i)$ and the shear wave velocity parameter $V_s(r_i)$, and a density transform based on a density mixing law can be used to compute the density parameter $\rho(r_i)$.

With regard to computing the resistivity parameter $R_t(r_i)$, Archie's Law is an empirical law attempting to describe ion flow (mostly sodium and chloride) in clean, consolidated sands, with varying intergranular porosity. Electrical conduction is assumed not to be present within the rock grains or in fluids other than water. Archie's law relates the in-situ electrical conductivity of sedimentary rock to its porosity and connate water saturation:

$$C_t = \frac{1}{a} C_w \phi^m S_w^n \quad (1)$$

Here, $\phi$ denotes the porosity, $C_t$ the electrical conductivity of the fluid saturated rock, $C_w$ represents the electrical conductivity of the connate water, $S_w$ is the water saturation, m is the cementation exponent of the rock (usually in the range 1.8-2.0 for sandstones), n is the saturation exponent (usually close to 2) and a is the tortuosity factor. Equation (1) can be reformulated to solve for electrical resistivity, $R_t$, as follows:

$$R_t = a\phi^{-m} S_w^{-n} R_w, \quad (2)$$

where $R_t$ is the fluid saturated rock resistivity, and $R_w$ is the connate water resistivity.

With regard to computing the compressional wave velocity parameter $V_p(r_i)$ and the shear wave velocity parameter $V_s(r_1)$, an effective medium rock physics model can be used for formations with complex mineralogy that are composed of multiple minerals and pore types (such as shaly sandstones or carbonates). By way of example, a Xu-White effective medium rock physics model may be used to compute the radial profiles of compressional wave velocity $V_p(r_i)$ and shear wave velocity $V_s(r_i)$. Alternate or additional models that could be applied include the Self-Consistent model and the Xu-Payne model.

The inputs to the Xu-White model are the water saturation parameter $S_w(r_i)$, porosity parameter $\phi(r_i)$, and the mineralogy defined by shear modulus $(\mu_{min})_i$, bulk modulus $(K_{min})_i$, density $(\rho_{min})_i$, and volume fractions $(x_{min})_i$ of each mineral $i = 1, \ldots, N_{min}$, in the rock in the interval of interest. An additional input to the Xu-White model is the pore shape, defined as the ratio of the minor axis to major axis of a spheroidal pore. The pore orientations have a uniform random distribution for an isotropic medium. A single, effective aspect ratio, denoted by $\alpha$, can be defined for all pores in the interval-of-interest. Increasing (or decreasing) the pore aspect ratio has the impact of stiffening (or softening) the rock. Consequently, different porosity types can be characterized by their effective pore aspect ratio. Compliant porosity types (e.g., microporosity) would have lower aspect ratio pores, whereas stiffer porosity types (e.g., macroporosity) would have higher aspect ratio pores. The effective pore aspect ratio is an output from the inversion workflow described later.

The Xu-White model computes effective bulk modulus $K_{dry}(r_i)$ and effective shear modulus $\mu_{dry}(r_i)$ of the dry rock by extending the Kuster-Toksoz model, which is only valid for rocks with small porosity such that $\phi/\alpha \ll 1$, to apply to rocks with larger porosity. This can be done by partitioning the porosity into P parts such that $\phi/(P\alpha) \ll 1$. The Kuster-Toksoz model is then applied iteratively for P iterations, where at each iteration, the background medium has effective moduli from the previous iteration and the porosity is $\phi/P$. The equations at each iteration are:

$$K_{dry}(r_i) - K_m = \frac{1}{3}(K_f - K_m)\frac{3K_{dry}(r_i) + 4\mu_m}{3K_m + 4\mu_m}\frac{\phi(r_i)}{P}T_{iijj} \quad (3a)$$

$$\mu_{dry}(r_i) - \mu_m = \frac{(\mu_f - \mu_m)}{5}\frac{6\mu_{dry}(r_i)(K_m + 2\mu_m) + \mu_m(9K_m + 8\mu_m)}{5\mu_m(3K_m + 4\mu_m)}\left(T_{ijij} - \frac{T_{ijij}}{3}\right)\frac{\phi(r_i)}{P} \quad (3b)$$

where $K_m$, $\mu_m$ are the bulk and shear modulus of the background medium, $K_f$, $\mu_f$ are the bulk and shear modulus of the pore fluid, and $T_{iijj}$, $T_{ijij}$ are scalars that depend on the pore aspect ratio $\alpha$ as defined in Appendix B of Xu-White (1995).

The above equations are applied with fluid bulk modulus $K_f$ and fluid shear modulus $\mu_f$ both set to zero to obtain the moduli of the dry rock. In the above equations, the moduli of the solid background for the first iteration is obtained from the moduli of the component minerals by a mixing law (e.g., Voigt average or Voigt-Reuss-Hill Average). For the Voight average:

$$K_m = \Sigma_{i=1}^{N_{min}} x_i (K_{min})_i, \quad (4a)$$

and $$\mu_m = \Sigma_{i=1}^{N_{min}} x_i (\mu_{min})_i. \quad (4b)$$

The dry bulk modulus $K_{dry}(r_i)$ and dry shear modulus $\mu_{dry}(r_i)$ of the rock could also be computed with the Self-Consistent effective medium model:

$$\Sigma_{i=1}^{N_{min}} x_i ((K_{min})_i - K_{dry}(r_i)) P_i + \phi(r_i)(K_f - K_{dry}(r_i)) P_f = 0, \quad (5a)$$

$$\Sigma_{i=1}^{N_{min}} x_i ((\mu_{min})_i - \mu_{dry}(r_i)) Q_i + \phi(r_i)(\mu_f - \mu_{dry}(r_i)) Q_f = 0, \quad (5b)$$

where $P_i$, $Q_i$ for $i = 1, \ldots, N_{min}$ are the geometric factors for each mineral that depend on the geometry assumed for the mineral grains, and $P_f$, $Q_f$ are the geometric factors for the fluid that depend on the pore aspect ratio $\alpha$. The expressions for the geometric factors are given in Table 4.8.1 of Mavko, et al., The Rock Physics Handbook: Tools for Seismic Analysis in Porous Media, p. 329 (1998), which is hereby incorporated by reference in its entirety. The geometric factors also depend on the effective dry rock moduli $K_{dry}(r_i)$, $\mu_{dry}(r_i)$. Thus, the above equations are coupled and are solved iteratively starting from an initial guess for the dry rock moduli, for example, by taking the Voight average or the Voight-Reuss-Hill average of the moduli of the minerals and fluid.

The effective bulk modulus $K_{eff}(r_i)$ and effective shear modulus $\mu_{eff}(r_i)$ moduli of the fluid saturated rock are then computed by Gassmann fluid substitution:

$$K_{eff}(r_i) = \qquad (6a)$$
$$K_{dry}(r_i) + \left(1 - \frac{K_{dry}(r_i)}{K_m}\right)^2 \bigg/ \left(\frac{\phi(r_i)}{K_f} + \frac{(1-\phi(r_i))}{K_m} - \frac{K_{dry}(r_i)}{K_m^2}\right), \text{ and}$$

$$\mu_{eff}(r_i) = \mu_{dry}(r_i). \qquad (6b)$$

The shear modulus of the pore fluid is zero (by definition), whereas the bulk modulus of a mixture of water, gas, and oil is obtained by Wood's Law:

$$K_f = \left(\frac{s_w(r_i)}{K_w} + \frac{s_g(r_i)}{K_g} + \frac{s_o(r_i)}{K_o}\right)^{-1} \qquad (7)$$

where $K_w$, $K_g$, $K_o$ are the bulk moduli of water, gas, and oil, respectively.

If gas is present in the pores, then an empirical mixing law can also be applied:

$$K_f = (K_w - K_g)S_w^3(r_i) + (K_o - K_g)S_o^3(r_i) + K_g. \qquad (8)$$

Here $S_o(r_i), S_g(r_i)$ are the oil and gas saturation in each pixel. The fluid saturations satisfy the constraint $S_w(r_i) + S_o(r_i) + S_g(r_i) = 1$. For an oil-bearing formation one can set $S_g(r_i) = 0$. For a gas-bearing formation, one can assume $S_g(r_i)$ is known, or can estimate it from the data using the workflow described later. Finally, the compressional wave velocity parameter $V_p(r_i)$ and shear wave velocity parameter $V_s(r_i)$ are computed as:

$$V_p(r_i) = \sqrt{\frac{K_{eff}(r_i) + \frac{4}{3}\mu_{eff}(r_i)}{\rho(r_i)}}, \text{ and} \qquad (9a)$$

$$V_s(r_i) = \sqrt{\frac{\mu_{eff}(r_i)}{\rho(r_i)}}. \qquad (9b)$$

With regard to computing the density parameter $\rho(r_i)$, a density mixing law may be applied. The density mixing law applied here is based on the volumetric average of the densities of the rock matrix and pore fluid as follows:

$$\rho(r_i) = (1-\phi(r_i))\Sigma_{i=1}^{N_{min}} x_i(\rho_{min})_i + \phi(r_i)(S_w(r_i)\rho_w + S_o(r_i)\rho_o + S_g(r_i)\mu_g) \qquad (10)$$

where $\rho_w$, $\rho_o$, $\rho_g$ are the densities of water, oil, and gas, respectively.

The parameters that represent the radial profile of various petrophysical properties of the formation at the interval-of-interest can be used as inputs to various tool simulators as shown in FIG. 1B. The tool simulators produce simulated log data for use in refining the formation model. In one embodiment, the various tool response simulators can process the resistivity parameter $R_t(r_i)$, the compressional wave velocity parameter $V_p(r_i)$, the shear wave velocity parameter $V_s(r_i)$, and the density parameter $\rho(r_i)$ to obtain simulated resistivity data, simulated sonic data, and simulated density data. Such simulated log data can then be used for comparison against corresponding measured log data and, in turn, used for refinement of the formation model, as described in greater detail below.

In one embodiment, the resistivity parameter $R_t(r_i)$ can be input to an electromagnetic forward model for computing simulated resistivity data. The forward model is designed based on a more general two-dimensional formation model with several layers in the vertical direction, where in each layer the properties are defined by a one-dimensional radial formation model. Thus formation properties can vary in both vertical and radial directions but are constant in the azimuthal direction. The magnetic permeability $\mu_m(r,z)$, conductivity $\sigma(r,z)$ and dielectric constant $\varepsilon(r,z)$ of the formation are functions of radius r and depth z only. For the induction resistivity tool, the transmitter generates a pure transverse electric field. The only nonzero component of the electric field is the azimuthal component $E_\phi$. From Maxwell's equations, it can be shown that $E_\phi$ satisfies the following partial differential equation:

$$\left(\mu_m \frac{\partial}{\partial r} \frac{1}{r\mu_m} \frac{\partial}{\partial r} r + \frac{\partial^2}{\partial z^2} r + \frac{\partial^2}{\partial z^2} + \omega^2 \mu_m \varepsilon\right) E_\phi = \qquad (11)$$
$$-i\omega\mu_m I\delta(r-r_0)\delta(z-z_0)$$

where the complex permittivity is $$\epsilon(r,z) = \epsilon_0\left(\epsilon_r(r,z) + \frac{i\sigma(r,z)}{\omega\epsilon_0}\right),$$

and l is current of the transmitter coil located at $(r_0, z_0)$.

To solve the above equation for the response at each receiver, a numerical mode-matching method (NMM) can be applied. The basic concept of the NMM method is to convert the two-dimensional problem into N one-dimensional radial problems (N is the number of layers in the vertical direction), and then perform mode matching at the layer boundaries. The first step in the NMM method is to find the eigenvalues and the eigenmodes in every layer by solving the homogeneous part of the governing equation. Note that inside each layer, $\mu_m$ and $\varepsilon$ are functions of z; hence, these eigenvalue problems are one-dimensional, and can be solved easily with a one-dimensional solver. If M basis functions are used for each layer, the partial differential equations for the eigenvalue problems can be converted into matrix eigenvalue equations of dimension M×M, which are easily solved by standard eigenvalue solvers. In this procedure, M eigenvalues and the corresponding M eigenmodes for each layer are obtained.

The field generated by a transmitter is then expressed in terms of a summation of the eigenmodes in each layer, with some unknown expansion coefficients. The expansion coefficients are called the reflection and transmission operators and are similar to the reflection and transmission coefficients in a one-dimensional layered medium. Recursive relations for these operators can be obtained by mode matching at the layer boundaries. Therefore, the above NMM method can effectively convert a two-dimensional problem into several one-dimensional problems, which significantly reduces computational time.

The compressional velocity parameter $V_p(r_i)$ and the shear velocity parameter $V_s(r_i)$ and the density parameter $\rho(r_i)$ may be input into a sonic forward model for computing simulated sonic data. The sonic data used in the inversion can consist of dispersion data for the wellbore-guided flexural wave excited by a dipole acoustic source. To simulate such flexural wave dispersion data, the response of the wellbore and one-dimensional radial formation model to excitation by a dipole source located at the center of the wellbore is considered. The wavefield in the wellbore satisfies the acoustic wave equation governing the wellbore fluid and includes the superposition of the direct wavefield from the source and the reflected wavefield from the wellbore-formation interface. Similarly, the wavefield in the formation includes an incoming and outgoing wavefield that satisfies the vector wave equation for an isotropic elastic medium in each pixel. The amplitude coefficients of the reflected wavefield in the wellbore, and the wavefield in each formation pixel, are determined by applying the relevant boundary conditions at each interface. Specifically, at the interface between the wellbore fluid and the first formation pixel (fluid-solid interface), the radial velocity and stress are continuous, while at the interface between any two formation pixels (solid-solid interface) the radial and tangential components of velocity and stress are continuous. This leads to a system of linear equations Mx=0 in the unknown amplitude coefficients x, where M is the so-called acoustic guidance matrix that depends on the radial profiles of compressional wave velocity parameter $V_p(r_i)$, the shear wave velocity parameter $V_s(r_i)$, and density parameter $\rho(r_i)$.

The wellbore acoustic wave spectrum can be shown to arise from the contribution of few poles and branchlines in the complex wavenumber plane. The wavefield associated with each pole corresponds to a wellbore-guided wave mode. The poles are defined by the axial wavenumbers k and frequency $\omega$ at which the determinant of the acoustic guidance matrix is zero, or $\text{Det}(M(k, \omega))=0$. The dispersion curve for each wave mode is obtained by tracking each pole over a frequency range of interest. The poles may be computed using a root-finding algorithm (e.g., Newton-Raphson algorithm) starting from a suitable initial guess. For the flexural wave mode, the initial guess at low frequencies is set to the shear wave velocity parameter $\overline{V}_s$ of the far-field. The initial guess at higher frequencies is obtained by linear extrapolation of the pole from the preceding frequency. The phase slowness of the mode at each frequency is defined as $k(\omega)/\omega$.

The sonic data also includes first-arrival times $TOF_j$ of the compressional headwave excited by a monopole acoustic source. The first-arrival times are measured at an array of receivers labelled j=1, . . . , M with source-receiver spacing $Z_j$. The data are simulated by a ray tracing algorithm that satisfies Snell's law at each pixel boundary. For the one-dimensional radial formation model, the first-arrival times can be computed analytically as follows. The geometry of ray propagation based on Snell's Law implies that a minimum source-receiver spacing $L_i^{min}$ is required to capture a ray that returns to the wellbore after reflection from the interface at $r_i$:

$$L_i^{min} = 2\left(\frac{r_{bh}}{\sqrt{\frac{V_p^2(r_i)}{V_{mud}^2} - 1}} + \sum_{j=1}^{i-1} \frac{(r_{j+1} - r_j)}{\sqrt{\frac{V_p^2(r_i)}{V_{mud}^2} - 1}}\right), \quad (12)$$

$$i = 1, \dots, N^{pixels}$$

where $V_{mud}$ is the wellbore mud velocity.

Thus the $j^{th}$ receiver will capture rays from at most K pixels where K satisfies $L_K^{max} < Z_j < L_{K+1}^{max}$. Ray paths for the captured ray from each pixel that has the shortest travel time are computed. The travel times $T_i$ of these rays are given by:

$$T_i = \frac{z_j}{V_p(r_i)} + 2\left(\frac{r_{bh}}{V_{mud}}\sqrt{1 - \frac{V_{mud}^2}{V_p^2(r_i)}} + \sum_{m=1}^{i-1} \frac{(r_{m+1} - r_m)}{V_p(r_m)}\sqrt{1 - \frac{V_p^2(r_m)}{V_p^2(r_i)}}\right), \quad (13)$$

$$i = 1, \dots, K$$

The first-arrival ray path corresponds to the ray from the above set with the smallest travel time. Thus the first-arrival time at the $j^{th}$ receiver is given by $TOF_j = \min(T_i, i=1, \dots, K)$. The first-arrival times can be converted to slownesses of the compressional headwave by subtracting first-arrival times of nearby receivers and dividing by the spacing between those receivers. The computed slownesses can be used as input data in the inversion workflow instead of first-arrival times because the slownesses are relatively less affected by errors in the wellbore radius and mud properties.

For a two-dimensional formation model with both radial and vertical variation of formation properties, the ray path corresponding to a first-arrival is computed numerically by a so-called shooting method. This is done by numerically solving the optimization problem of minimizing the ray travel time over ray paths corresponding to different initial direction of the source ray.

The density parameter $\rho(r_i)$ can be input to the density forward model, which takes a weighted average of the density in each pixel to obtain simulated density data $\rho$ as follows:

$$\rho = \sum_{i=1}^{Npixels} w_i \rho(r_i), \quad (14a)$$

and $$\sum_{i=1}^{Npixels} w_i = 1. \quad (14b)$$

The density data $\rho$ is the data after applying the standard correction for possible presence of mudcake between the tool detector and formation. The weights $w_i$ represent the normalized radial sensitivity of the data to formation density. Here the weights are chosen so as to match the normalized radial sensitivity of the data determined from Monte-Carlo modeling of the density tool response. The radial sensitivity decays such that approximately 50% of the cumulative radial sensitivity is from the formation in the first two inches away from the wellbore, and approximately 100% of the cumulative radial sensitivity is from the formation within the first six inches away from the wellbore.

The simulated resistivity data, simulated sonic data, and simulated density data can then be compared against the corresponding measured log data from the field log. If the simulated log data and measured log data are discrepant, the formation model is refined (or tuned) and the process in FIG. 1B is repeated until the simulated log data matches the measured log data (within some predefined threshold tolerance). The resultant final formation model for one or more intervals-of-interest within the well (or wellbore) can then be output for evaluation (for example, as part of reservoir analysis).

Figure 1C:
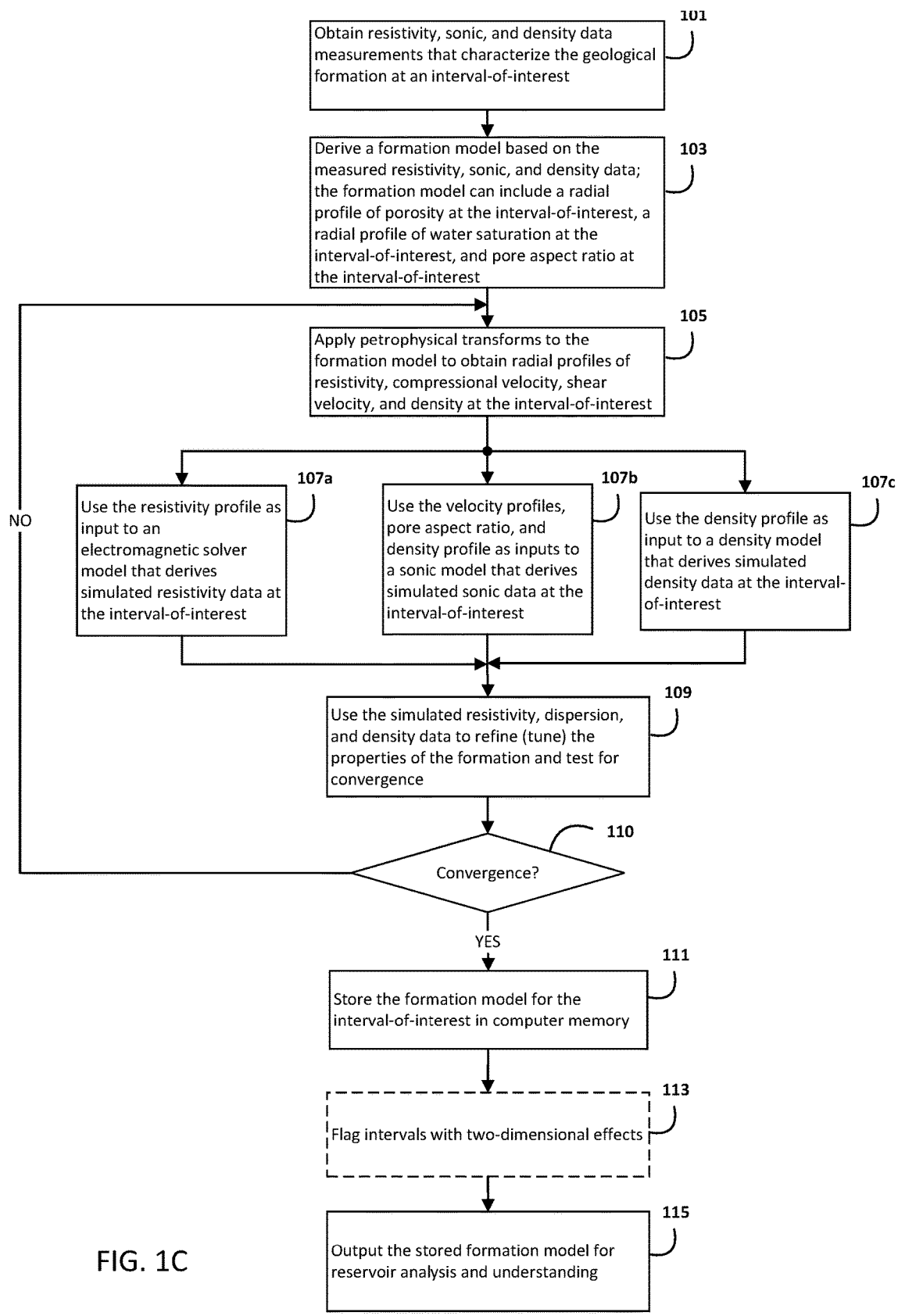
FIG. 1C shows a forward modeling workflow that incorporates the forward modeling method of FIG. 1B.

An embodiment of a workflow employing the method of FIG. 1B is shown in FIG. 1C. At block 101, for a specific interval-of-interest in a well (or wellbore), resistivity data, sonic data, and density data that characterize the formation at the specific interval-of-interest are obtained from well logging operations within the well (or wellbore). In one embodiment, the resistivity data can be wellbore corrected and rotated to true north. The measurements are acquired at different source frequencies and at different spacing between the source and receiver. The measurements from different spacings and frequencies correspond to different channels (identified by a channel index). The sonic data can be generated by processing the measured waveforms with an extended Prony method to extract dispersion data for various wellbore-guided wave modes, followed by a labeling algorithm to extract the dispersion data for the flexural wave mode. Typically, dispersion data for the flexural wave mode between 1 kHz to 10 kHz is used in the inversion workflow. In various embodiments the sonic data can include the compressional wave velocity log and shear wave velocity log obtained by Semblance-Time-Coherence (STC) processing of the measured waveforms. In various embodiments, the sonic data is generated with multishot, subarray processing to increase the vertical resolution of the data. In another embodiment, sonic data includes the transit times of the first arrival of the compressional headwave extracted from the waveforms measured at each receiver of the sonic logging tool. The measurements at different receivers corresponds to different channels (identified by a channel index). Also, the resistivity data, the sonic data and the density data obtained from well logging operations can be made accessible for use in populating the parameters of the initial formation model, as described in greater detail below.

Figure 2:
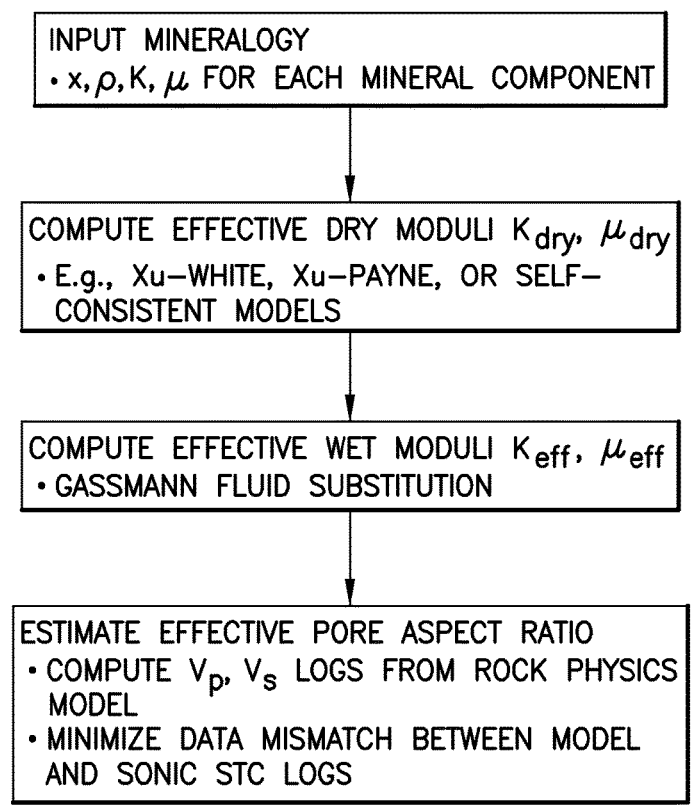
FIG. 2 shows a workflow for estimating the pore aspect ratio in accordance with one embodiment of the present disclosure.

At block 103, an initial formation model for the interval-of-interest is derived based on the resistivity data, sonic data, and density data measured in block 101 for the interval-of-interest. In one embodiment, an initial radially homogeneous formation model is generated by techniques known in the art. For example, an initial radially homogeneous porosity can be derived from the density log, and the density mixing law assuming $S_w$=100%. An initial radially homogeneous water saturation can be derived from the deep DOI resistivity log, porosity, and a resistivity-saturation transform (e.g., based on Archie's Law). The mineral volume fractions in the interval of interest can be obtained by techniques known in the art, such as by analysis of data from a geochemical logging tool. The corresponding bulk modulus, shear modulus, and density for each mineral component can be extracted from a database of standardized laboratory measurements. As shown in FIG. 2, the initial value of the pore aspect ratio may be estimated for the interval-of-interest by minimizing a cost-function defined as the squared $L_2$-norm error between the compressional wave velocity and shear wave velocity from the effective medium rock physics model, and the compressional wave velocity and shear wave velocity from STC processing. A line-search algorithm is used for the minimization. Parameters for use in the resistivity-saturation transform, such as a connate water resistivity, cementation exponent and a saturation exponent, may be determined by techniques known in the art, such as based on measurements from cores obtained from the geological formation at or near the interval-of-interest.

At block 105, petrophysical transforms as described above are applied to the modeled values of water saturation, porosity, and pore aspect ratio to obtain radial profiles of resistivity, compressional wave velocity, shear wave velocity, and density of the formation at the interval-of-interest.

At block 107a, the radial profile of resistivity of the formation at the interval-of-interest can be used as an input to the electromagnetic forward model as described above that derives simulated resistivity data for the interval-of-interest.

At block 107b, the radial profiles of compressional wave velocity, shear wave velocity, and density of the formation at the interval-of-interest as well as the pore aspect ratio of the formation at the interval-of-interest can be used as inputs to a sonic forward model as described above that derives simulated sonic data for the interval-of-interest.

At block 107c, the radial profiles of density of the formation at the interval-of-interest can be used as an input to a density forward model to derive simulated density data for the interval-of-interest.

At block 109, the simulated resistivity data of block 107a, the simulated sonic data of block 107b, and the simulated density data of block 107c are compared to the corresponding measured log data to determine if such data match within a predefined threshold, i.e., if the simulated log data and measured log data converge. If the simulated data and measured data do not match (e.g., there is no convergence), then the formation model is refined with new values and blocks 105 to 109 are repeated until the simulated log data matches the measured log data (e.g., there is convergence). If the simulated log data matches the measured log within the threshold (there is convergence as noted by YES at block 110), then the resultant formation model values for the interval-of-interest are stored into computer memory at block 111.

The inversion workflow is typically applied to a sequence of intervals, where for each interval, the formation properties are assumed to be vertically homogeneous as described before. However, if the true formation in this sequence of intervals has vertical variation in formation properties within the vertical resolution of the logging tool, then the results from the inversion workflow may be biased on account of ignoring the two-dimensional nature of the true formation. Consequently, at optional block 113, intervals where the inversion output has a bias because of two-dimensional effects can be identified and flagged. Specifically, a two-dimensional formation model, with both radial and vertical variation of water saturation and porosity, can be created by stacking the one-dimensional radially varying formation models obtained as output from the inversion over a sequence of intervals. Simulated data that includes the two-dimensional effect can then be generated by using this created two-dimensional formation model as input to the tool response simulators. The simulated data for the two-dimensional formation model is compared with the simulated data from the inversion. Any intervals where the simulated data for the two-dimensional formation model differs significantly (e.g., beyond a predetermined threshold) from the simulated data from the inversion indicates that two-dimensional effects are significant in those intervals. Accordingly, the output from the inversion in those intervals can be flagged as requiring correction for two-dimensional effects.

At block 115, the stored data that represents the formation model for one or more intervals-of-interest can be output for analysis, such as for reservoir analysis and understanding.

Inversion Workflow

Figure 3:
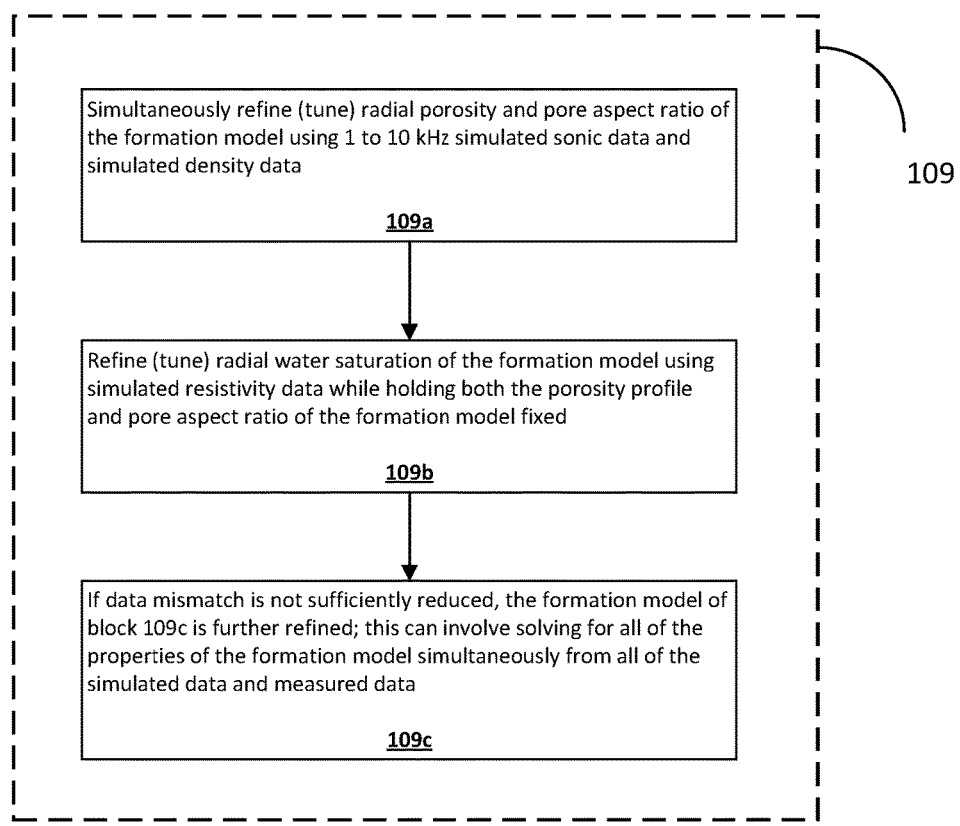
FIG. 3 illustrates an embodiment of joint inversion processing that can be part of the workflow of FIG. 1C in accordance with one embodiment of the present disclosure.

FIG. 3 shows an embodiment of further details of block 109 in FIG. 1C. Specifically, block 109 is shown including a plurality of sub-blocks 109a and 109b that together carry out a joint, inversion-based solution of the formation model parameters. In the sub-blocks 109a and 109b, the simulated data is used to tune the formation model for the interval-of-interest based on a comparison between the measured log data and the simulated log data for the interval-of-interest.

In block 109a, the pore aspect ratio of the formation at the interval-of-interest and the radial profile of porosity of the formation at the interval-of-interest can be simultaneously solved from the measured and simulated density data and the measured and simulated sonic data for the flexural wave mode in the interval-of-interest by minimizing a cost-function defined as the sum of the sonic data mismatch (e.g., defined as squared $L_2$-norm error between the measured and simulated sonic data that falls within the frequency band between 1 to 10 kHz for the interval-of-interest) and density data mismatch (e.g., defined as squared $L_2$-norm error between the measured and simulated density data for the interval-of-interest).

In block 109b, the radial profile of water saturation of the formation at the interval-of-interest can be solved from the simulated and measured resistivity data for the interval-of-interest while the porosity profile and pore aspect ratio of the formation at the interval-of-interest are held fixed. Such processing can involve minimizing the resistivity data mismatch (e.g., defined as squared $L_2$-norm error between the measured and simulated resistivity data for the interval-of-interest). To reduce non-uniqueness, a smoothness regularization term can be added to the cost-function in blocks 109a and 109b. The minimization algorithm may be Gauss-Newton with line-search, box-constraints, and adaptive choice of regularization parameter.

In block 109c, the formation model property values obtained from the blocks 109a and 109b may be further refined, for example, by solving for all the formation model property values simultaneously from some or all the data. This is done by minimizing a cost-function defined as the sum of the sonic data mismatch, density data mismatch, and resistivity data mismatch.

Various other properties of the formation can be determined from the finally determined values of the formation model, e.g., radial profiles for water saturation and porosity, and the pore aspect ratio.

The present disclosure describes the inversion-based workflow and shows results, by way of example, for noisy simulated data for an oil-bearing carbonate formation drilled with oil-based mud. The example shows that use of sonic data and resistivity data in the joint inversion is sufficient to recover radial saturation and porosity profiles if pore aspect ratio can be obtained accurately from another source. However, where the pore aspect ratio is unknown, the inclusion of density data into the joint inversion improves the evaluation by enabling reconstruction of unknown pore aspect ratio along with the radial saturation and porosity profiles. The radial profiles characterize the near-wellbore alteration and provide accurate far-field properties extending several feet into the formation, consistent with the radial DOI of the sonic and resistivity data.

Measurement Sensitivities

Figure 4:
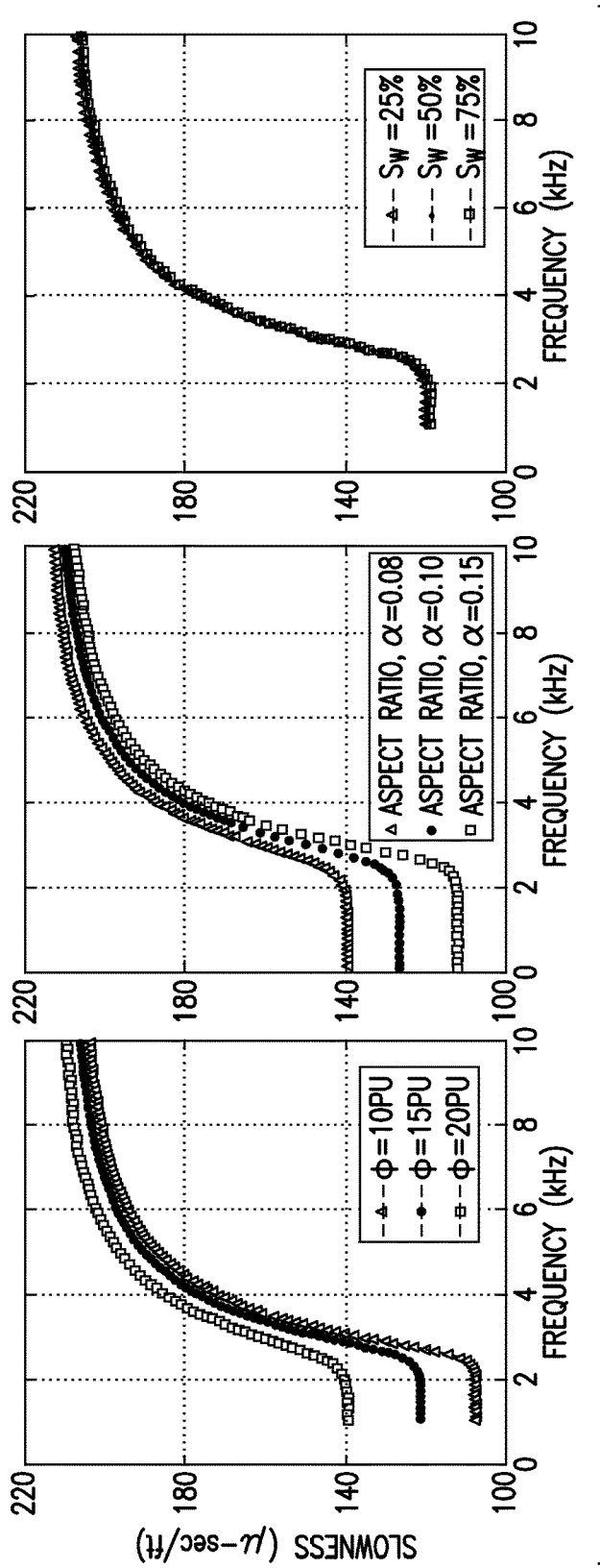
FIG. 4 includes three plots that show the sensitivity of sonic data to porosity, pore aspect ratio, and water saturation in accordance with one embodiment of the present disclosure.
Figure 5:
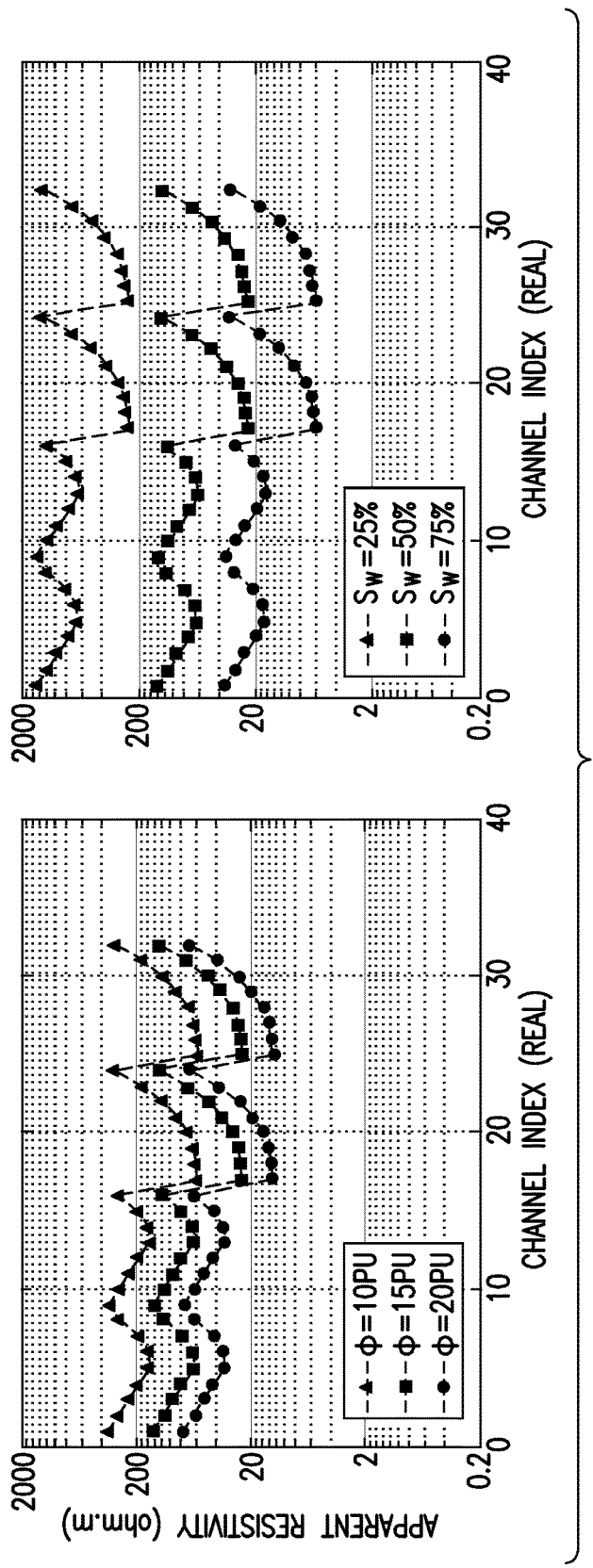
FIG. 5 includes two plots that show the sensitivity of array-induction (resistivity) data to porosity and water saturation in accordance with one embodiment of the present disclosure.
Figure 6:
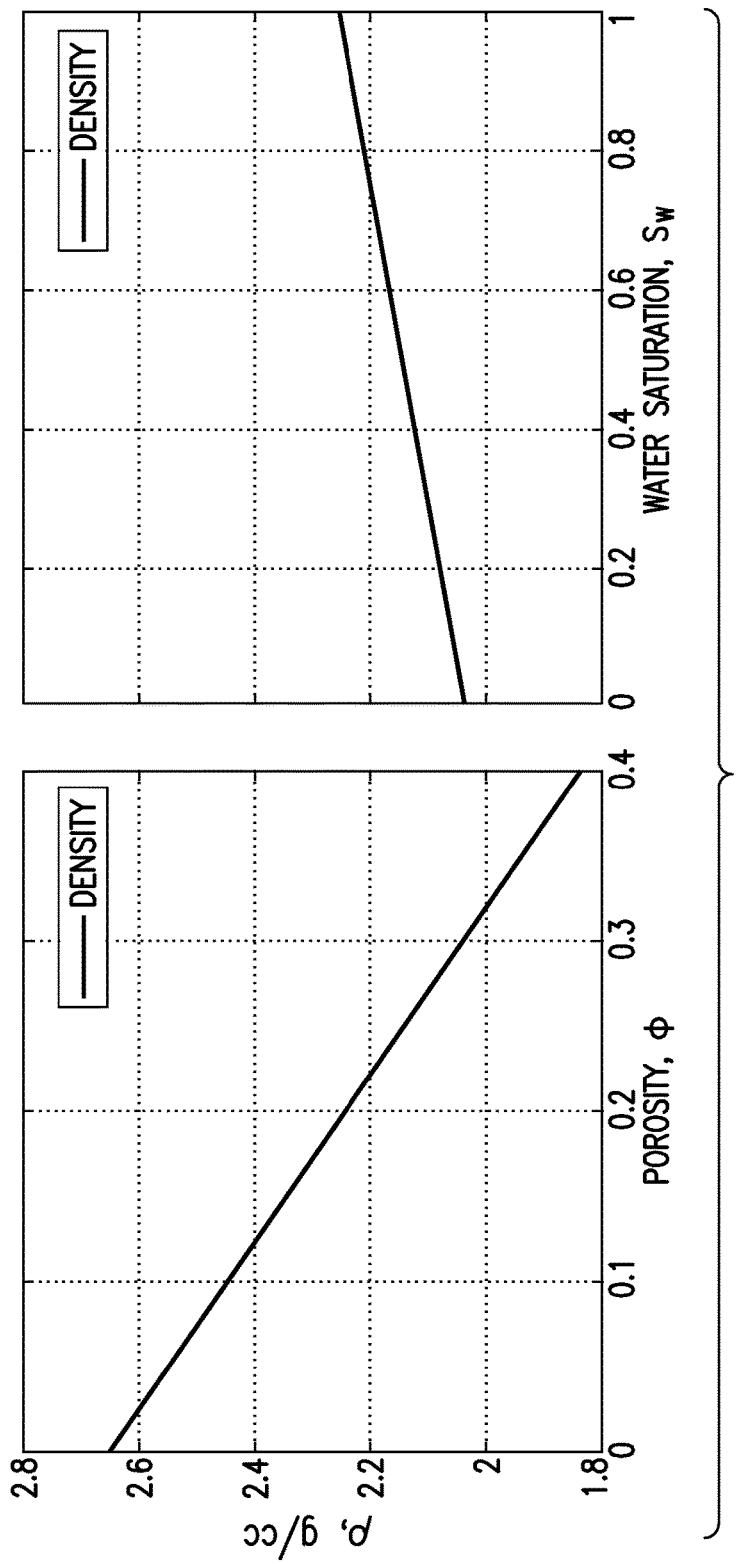
FIG. 6 includes two plots that show the sensitivity of density data to porosity and water saturation in accordance with one embodiment of the present disclosure.

In the example below, the sensitivities of the measurements to the formation parameters of interest are analyzed using a reference formation, which may be used as a calibration standard to validate the workflow described above. The reference formation for the example is a carbonate (75% calcite, 25% quartz) formation that contains an oil-water mixture with 50% water saturation in pores with a known aspect ratio of 0.1 and a porosity of 0.15. FIGS. 4, 5, and 6 illustrate the sensitivity of sonic data, resistivity data, and density data to water saturation, pore aspect ratio, and porosity. The simulated data in FIGS. 4, 5, and 6 were generated using tool response simulators (e.g., forward models) in conjunction with the aforementioned petrophysical transforms, specifically, Archie's Law, the Xu-White rock physics model, and the density mixing law, as discussed hereinabove.

FIG. 4 includes three plots that show the sensitivity of sonic data to porosity, pore aspect ratio, and water saturation in accordance with one embodiment of the present disclosure. The plots in FIG. 4 show that the sonic data (slowness of the flexural wave mode for different frequencies) is sensitive to porosity and pore aspect ratio, with greater sensitivity at lower frequencies. Also, the plots in FIG. 4 show that the sonic data (slowness of the flexural wave mode for different frequencies) has weak sensitivity to water saturation across all of the frequencies plotted. The weak sensitivity to water saturation is consistent with the theory that the flexural wave is mainly sensitivity to formation shear wave velocity, which is weakly sensitive to water saturation through changes in pore fluid density. In contrast to the trends of FIG. 4, as shown in FIG. 5, the resistivity is sensitive to both porosity and water saturation across all channels plotted. The sensitivity of the resistivity data is governed by the parameters in Archie's law. FIG. 6 illustrates the sensitivity of formation density to porosity and water saturation. The density is mainly sensitive to porosity with a weak sensitivity to water saturation. Furthermore, the density is independent of pore aspect ratio, as shown by the density mixing law. Consequently, the shallow DOI of the density data (1 to 2 inches into the well or wellbore) fixes the porosity near the well or wellbore, which allows to decouple the effects of porosity and pore aspect ratio on the high-frequency part of the sonic data. Therefore, it will be appreciated that the robustness of the inversion can be improved through a workflow where initial estimates of the radial porosity and pore aspect ratio for the one-dimensional radial formation model are determined from the measured sonic data and measured density data, which are held fixed when estimating radial water saturation from the measured resistivity data. The formation model obtained from the sequential inversion can be refined by simultaneously solving for all of the parameters using all the data.

Simulated Data Examples

The inversion workflow described with reference to FIG. 1C is applied to noisy synthetic data generated for several different oil-bearing carbonate formations that are drilled with oil-based mud and that have known well or wellbore parameters shown in Table 1, those parameters being used as calibration parameters for this example. The petrophysical transforms used in the inversion are the Xu-White effective medium rock physics model and Archie's law. The rock matrix for the examples has 75% calcite and 25% quartz composition. The elastic moduli and density for the mineral and fluid components are in Table 2. Parameters for Archie's law are a=1, m=2.2, n=3.4, and $R_w$=0.03 ohm·m, and the pores of the rock have an aspect ratio of 0.1. These parameters are relevant to an oil-bearing carbonate formation.

TABLE 1

| Well or Wellbore parameters for the inversion examples | |
|---|---|
| Well or Wellbore diameter | 0.31 m |
| Mud density | 1.00 g/cm³ |
| Mud slowness | 205 μ-sec/ft |

TABLE 2

| Elastic moduli and density for different mineral and fluid components | | | |
|---|---|---|---|
| Component | Bulk Modulus | Shear Modulus | Density |
| Quartz | 37.0 GPa | 44.0 GPa | 2.65 g/cm³ |
| Calcite | 76.7 GPa | 32.3 GPa | 2.71 g/cm³ |

TABLE 2-continued

Elastic moduli and density for different mineral and fluid components

| Component | Bulk Modulus | Shear Modulus | Density |
|---|---|---|---|
| Water | 2.74 GPa | — | 1.05 g/cm³ |
| Oil | 2.04 GPa | — | 0.75 g/cm³ |

Figure 7:
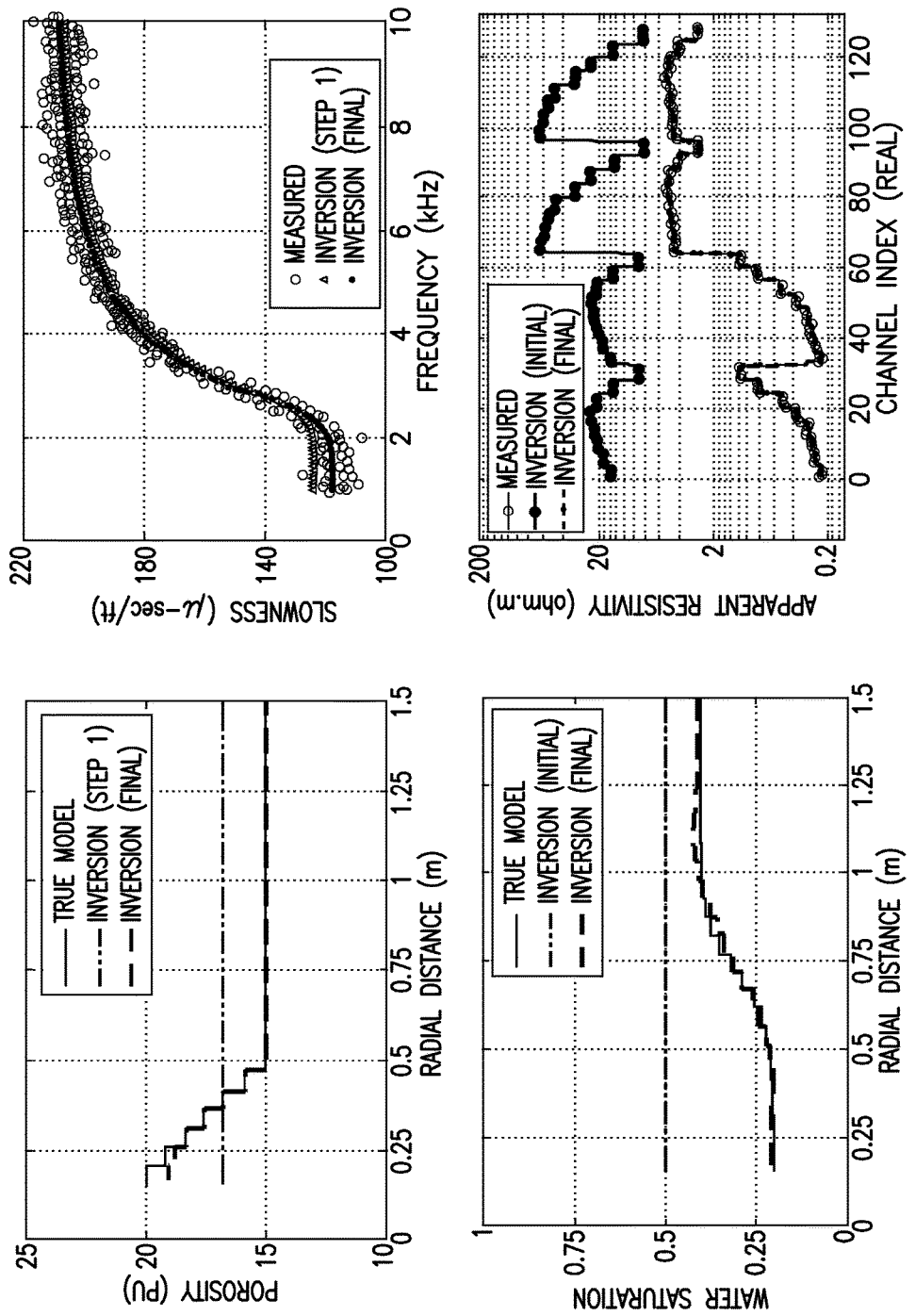
FIG. 7 includes four plots that show inversion results integrating sonic and resistivity data (assuming pore aspect ratio is accurately known) in accordance with one embodiment of the present disclosure.

FIG. 7 shows a first example that considers the case of mechanical rock breakdown leading to increased porosity of 20 p.u. at the surface of the well or wellbore that linearly decreases to a far-field porosity of 15 p.u. The alteration zone extends one diameter of the well or wellbore away from the well or wellbore. The invasion profile is a monotonic ramp invasion. The pore aspect ratio is accurately known and only sonic and resistivity data (but not density data) are used in the inversion. As shown in FIG. 7, the inversion recovers the true far-field water saturation and porosity, while also providing good reconstructions of the alteration zones.

Figure 8:
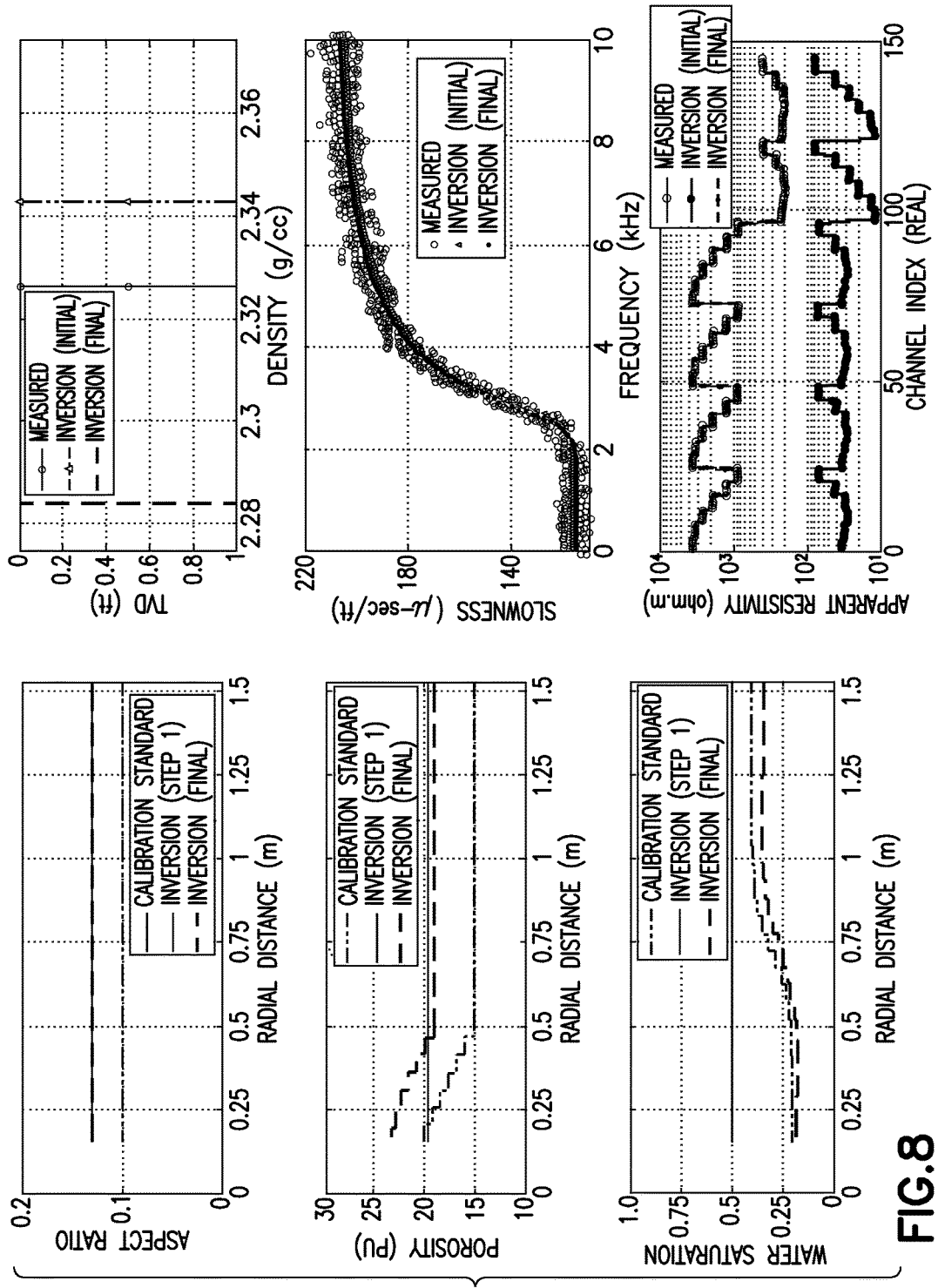
FIG. 8 includes six plots that show inversion results integrating sonic and resistivity data, assuming a pore aspect ratio from preprocessing, in accordance with one embodiment of the present disclosure.

FIG. 8 shows a second example where only sonic and resistivity data (but not density) are used in the inversion. However, unlike in FIG. 7, in the second example, the pore aspect ratio is not accurately known and an estimate of the pore aspect ratio from the preprocessing blocks 101 to 103 is used and is held fixed throughout the inversion beginning from blocks 105 to 110 of the workflow of FIG. 1C. However, the pore aspect ratio from the preprocessing blocks 101 to 103 has an error because the porosity used in the preprocessing blocks 101 to 103 is derived from the density log, which samples the mechanically damaged region close to the wellbore, because of the shallow DOI of the density measurement. Consequently, although the porosity profile reconstructed by the inversion shows an alteration zone, the error in the pore aspect ratio causes the porosity profile to be uniformly biased such that the far-field porosity matches the porosity from the density log. Also, at the end of the inversion, there is a large error in the simulated density log, because of the bias in the reconstructed porosity in the damaged zone.

Figure 9:
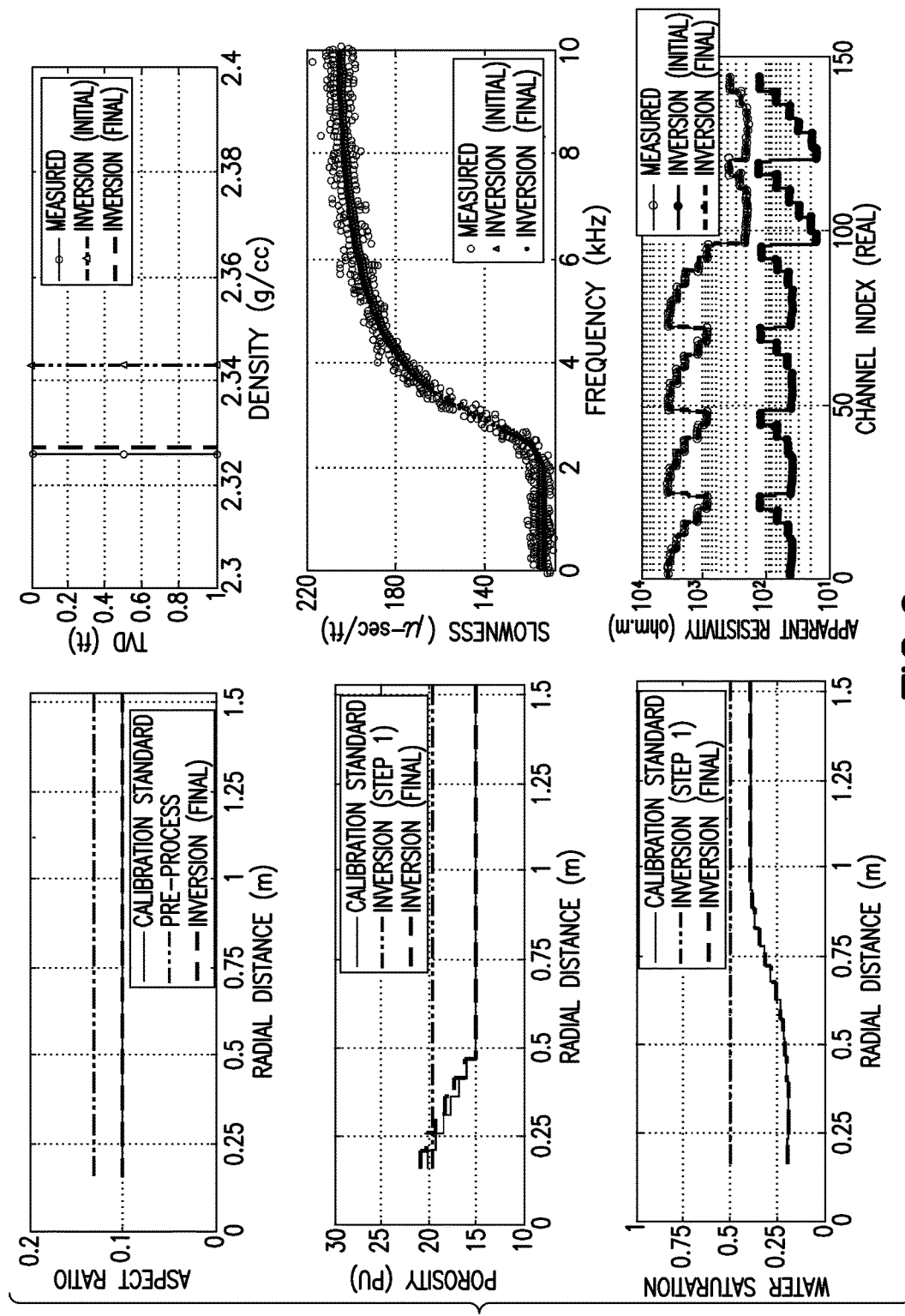
FIG. 9 includes six plots that show inversion results integrating sonic, resistivity, and density data, and solving for the pore aspect ratio and radial profiles in the inversion, in accordance with one embodiment of the present disclosure.

FIG. 9 shows a third example where sonic data and resistivity data, along with density data, are used in the inversion, and the pore aspect ratio is solved for along with the radial profiles of water saturation and porosity. Unlike the data from the example in FIG. 8, FIG. 9 shows that the inversion converges to the known pore aspect ratio, and radial profiles for water saturation and porosity. The density log for the reconstructed model agrees well with the measured density log. The results shown in FIG. 9 illustrate that the use of density data in the workflow, along with sonic and resistivity data, and solving for pore aspect ratio in the inversion helps to improve the estimate of far-field porosity and pore aspect ratio even if near-wellbore mechanical damage biases the porosity from the density measurement.

Figure 10:
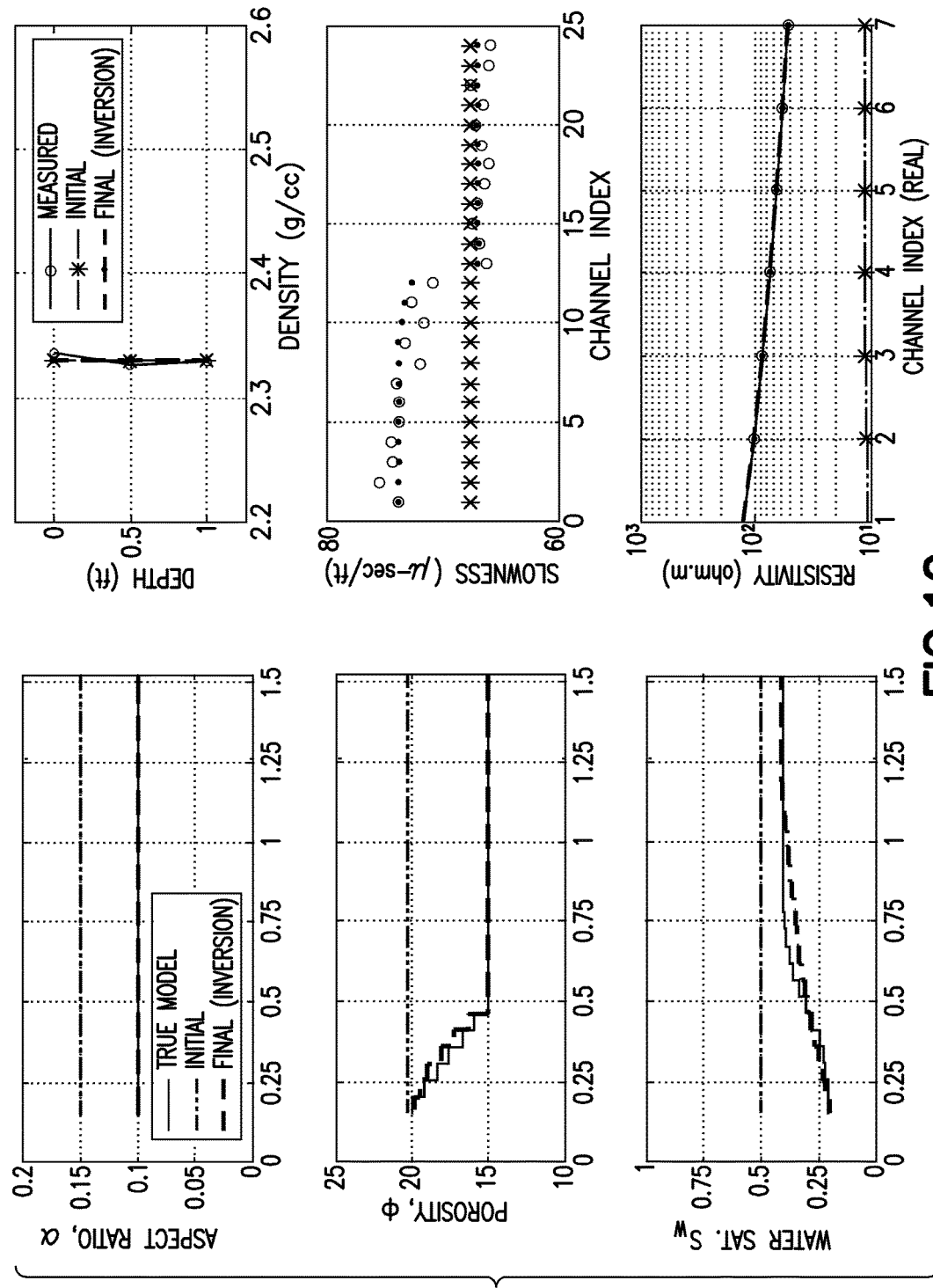
FIG. 10 includes six plots that show inversion results integrating sonic, resistivity, and density data, and solving for the pore aspect ratio and radial profiles in the inversion, in accordance with one embodiment of the present disclosure.

FIG. 10 shows six plots that show inversion results of a fourth example integrating sonic, resistivity, and density data, and solving for the pore aspect ratio and radial profiles in the inversion, in accordance with one embodiment of the present disclosure. In this example, the sonic data consists of first arrival times (or slownesses) of the compressional headwave. The results show that the inversion can solve for the pore aspect ratio, and radial profiles of water saturation and porosity from the sonic data, resistivity data, and density data.

Figure 11:
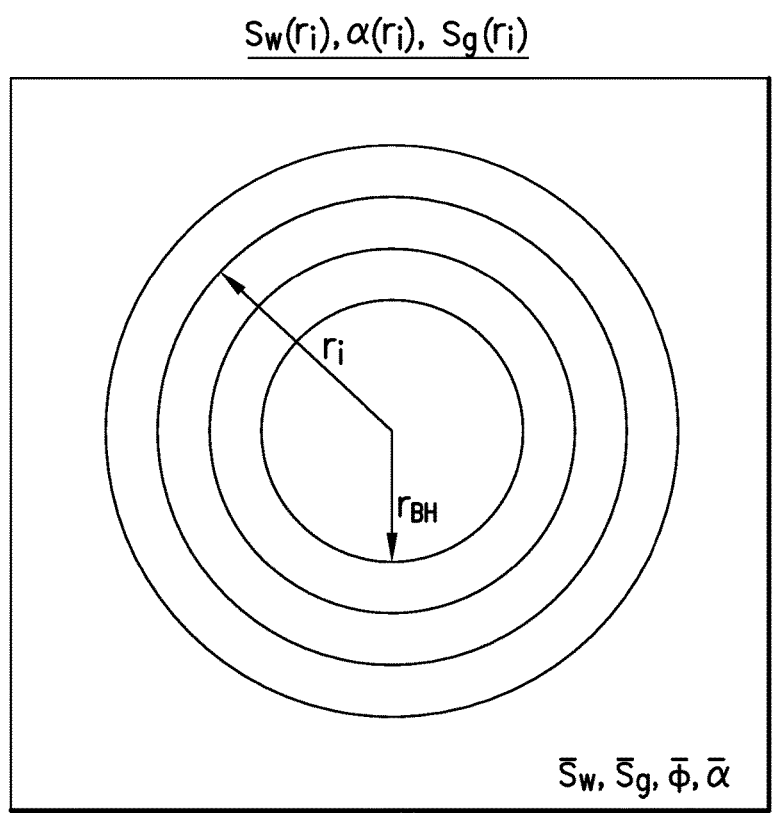
FIG. 11 illustrates another example of a formation model.

Another formation model is shown in FIG. 11. In contrast to the formation models described earlier, in the formation model shown in FIG. 11, the porosity, $\phi$, is assumed to be constant whereas the pore aspect ratio, $\alpha$, can vary in each pixel. In addition, the formation model also includes radial variation of the gas saturation, $S_g$. The gas saturation $S_g$ in a pixel at radius $r_i$ is denoted by $S_g(r_i)$ and the far-field gas saturation is denoted by $\overline{S}_g$. The water saturation $S_w$ in a pixel at radius $r_i$ is denoted by $S_w(r_i)$ and the far-field water saturation is denoted by $\overline{S}_w$. In this model, mechanical damage is represented by radial variation in pore aspect ratio, $\alpha$, rather than porosity, $\phi$. Note that the oil saturation in each pixel, denoted by $S_o(r_i)$, is determined from the constraint that $S_w+S_o+S_g=1$. The forward modeling framework described above in connection with FIG. 1B, may also be used in conjunction with the formation model in FIG. 11.

Figure 12:
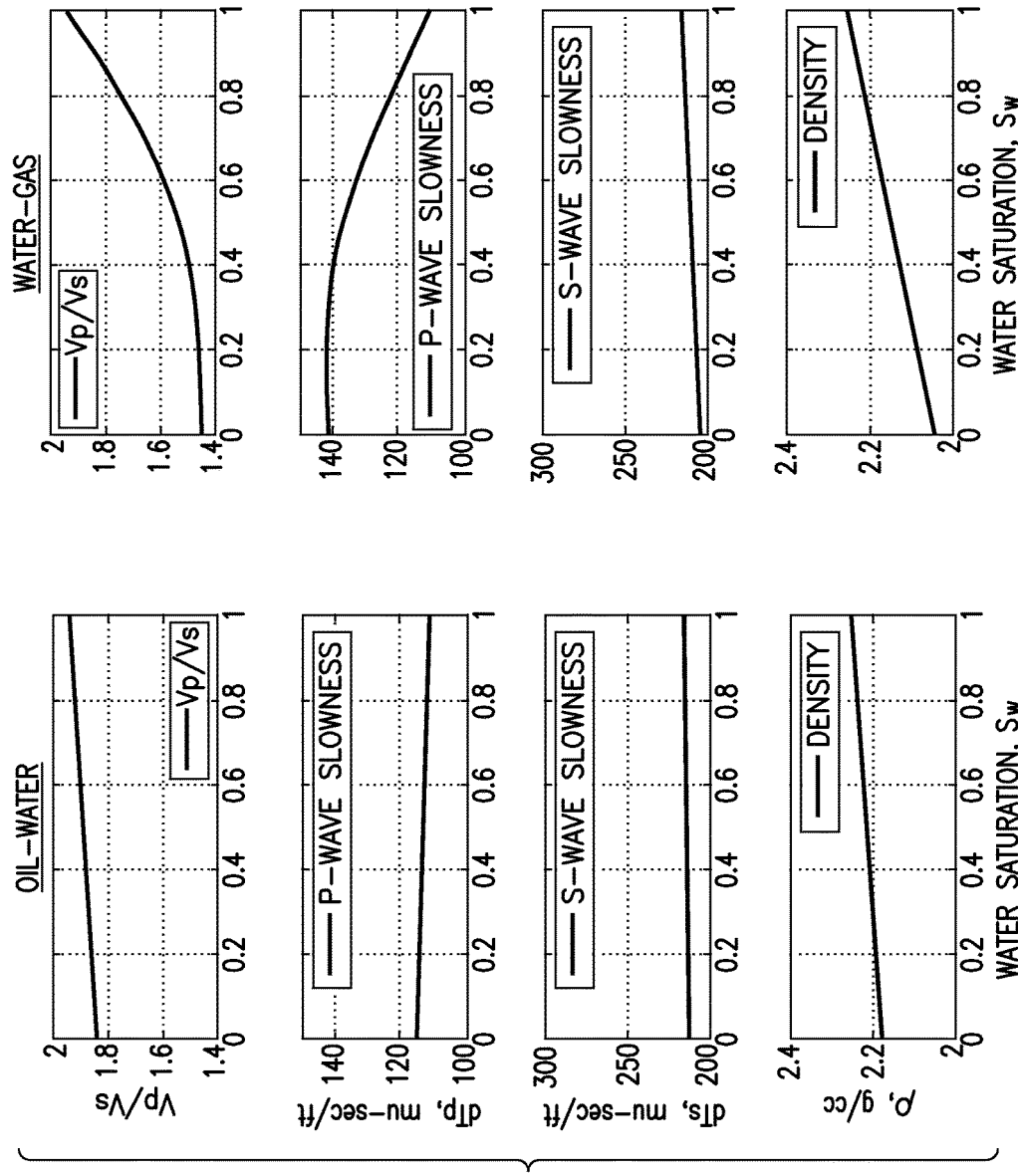
FIG. 12 shows the sensitivity of elastic properties of the formation to water saturation, $S_w$, as governed by the Xu-White rock physics model, for formations containing a mixture of oil and water or a mixture of gas and water in the pores.

FIG. 12 shows an example of the sensitivity of elastic properties of the formation to water saturation, $S_w$, as governed by the Xu-White rock physics model, discussed above. In the example, the formation is 100% quartz with porosity of 25% and pore aspect ratio of 0.05. The first column of graphs (on the left in FIG. 12) shows the sensitivity when the pores contain a mixture of oil and water. The second column of graphs (on the right in FIG. 12) shows the sensitivity when the pores contain a mixture of gas and water. The graphs illustrate that the compressional wave slowness (or P-wave slowness) is more sensitive to water saturation for formations containing gas. This is consistent with the fact that P-wave slowness of gas is significantly greater than P-wave slowness of either water or oil, whereas the latter have similar P-wave slowness. Consequently, measurements sensitive to P-wave slowness of the formation, such as the first arrivals of a compressional headwave, could be used to estimate proportion of gas in the formation.

A comparison of the graphs in FIG. 12 also shows that the formation density is more sensitive to water saturation for formations containing gas, again because density of gas is much smaller than density of water, whereas density of oil and water are relatively similar. Thus density data could also be used to distinguish the presence of gas. On the other hand, the shear wave slowness (or S-wave slowness) is weakly sensitive to changes in water saturation through changes in the pore fluid density and is therefore not useful for characterizing the pore fluid.

Figure 13:
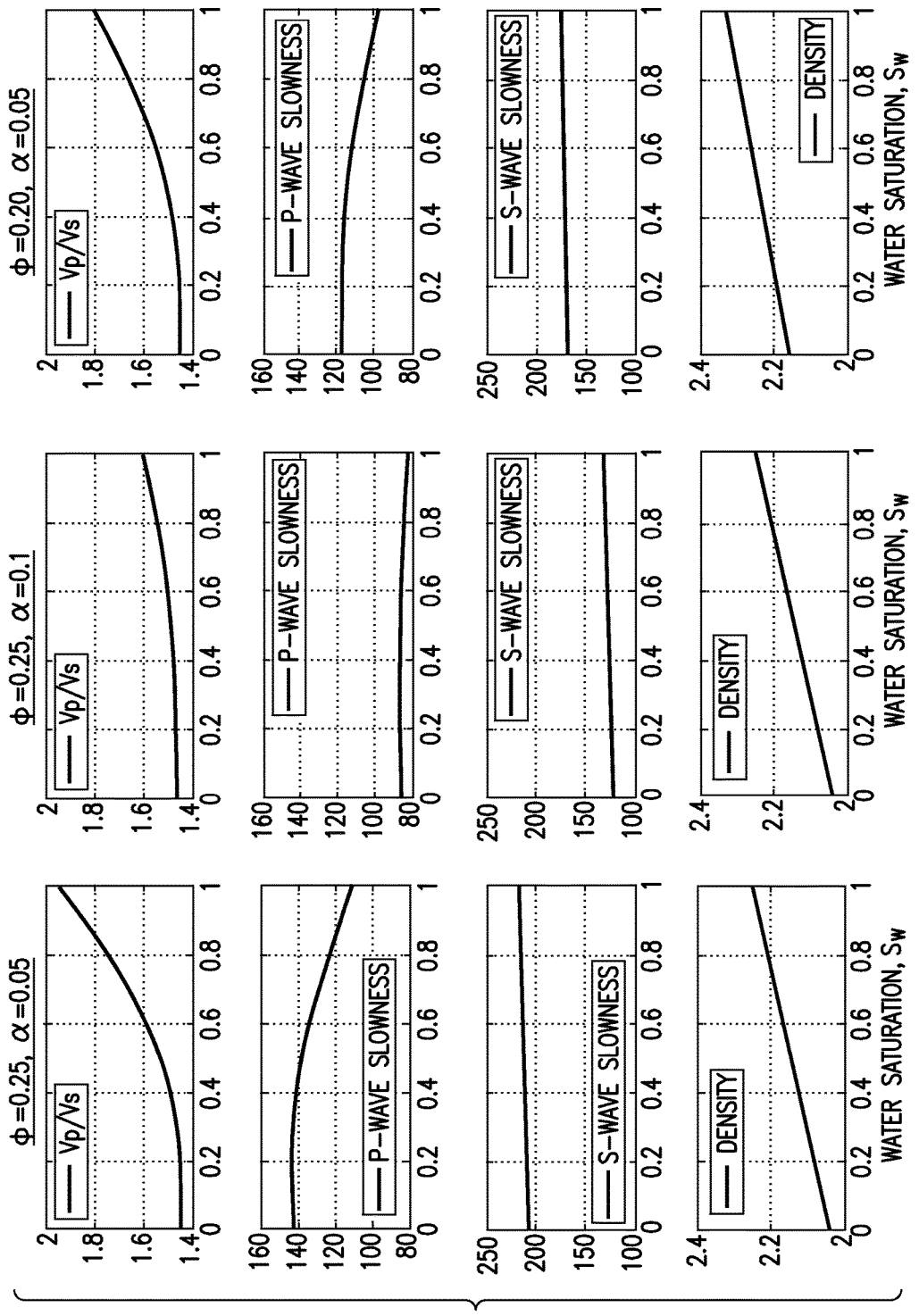
FIG. 13 shows the sensitivity of elastic properties of the formation to water saturation, $S_w$, as governed by the Xu-White rock physics model, for three formations with different porosity and pore aspect ratio (all the formations contain a mixture of gas and water in the pores)

FIG. 13 shows an example of the sensitivity of the elastic properties of the formation to water saturation $S_w$, as governed by the Xu-White rock physics model. In these examples, one formation has a porosity of 25% and pore aspect ratio of 0.05 (graphs in the first column of graphs in FIG. 13), another formation has a porosity of 25% and pore aspect ratio of 0.1 (graphs in the second column of graphs in FIG. 13) and a third formation has a porosity of 20% and a pore aspect ratio of 0.05 (graphs in the third column of FIG. 13). All the formations are 100% quartz with a mixture of gas and water in the pores. The graphs show that the sensitivity of the density and P-wave velocity to water saturation is enhanced by either increasing porosity or decreasing the pore aspect ratio. Consequently, measurements sensitive to the density or P-wave velocity may be more effective at distinguishing gas in formations that have higher porosity or thin, elongated pores (i.e., low aspect ratio).

Figure 14:
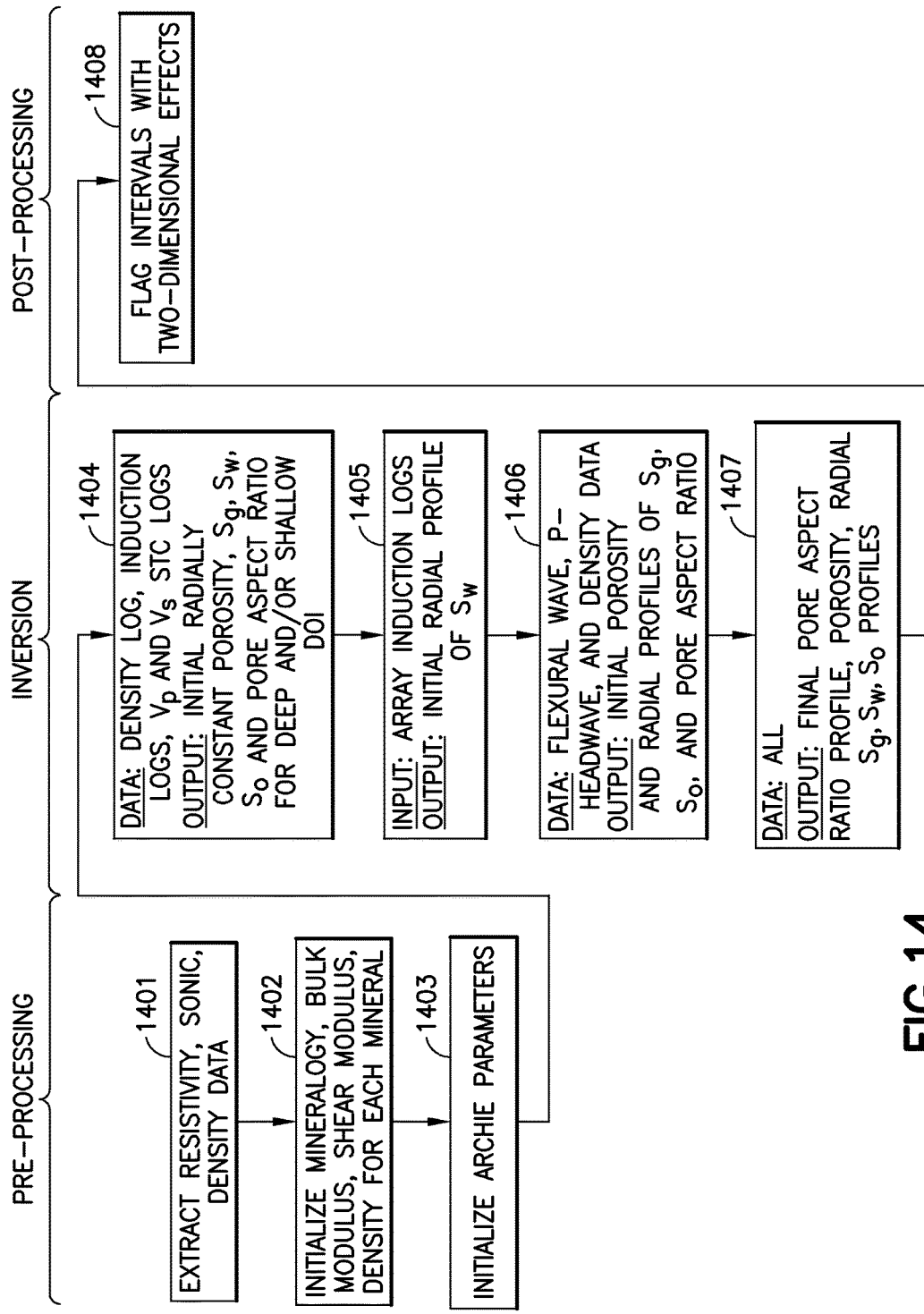
FIG. 14 shows an inversion workflow that may use the modeling framework of FIG. 1B to solve the model of FIG. 11.

An inversion workflow that is shown in FIG. 14 uses the modeling framework of FIG. 1B to solve the model of FIG. 11. Blocks 1401 to 1403 are preprocessing blocks. At block 1401 resistivity, sonic data, and density data are extracted. At block 1402 mineral volume fractions, elastic moduli of each mineral, and density of each mineral are fixed. In block 1403, the Archie parameters are fixed.

Blocks 1404 to 1407 are inversion blocks. At block 1404 an initial model of radially constant porosity, gas saturation, water saturation, oil saturation, and pore aspect ratio is estimated from the density data, resistivity data, and sonic STC logs. The radially constant model can be estimated separately for the shallow and deep DOI logs. At block 1405, with the formation properties from block 1404 fixed, an initial model of radially varying water saturation is estimated from the resistivity data. At block 1406, with the water saturation from block 1405 fixed, the porosity, radial profile of gas saturation, radial profile of oil saturation, and radial profile of pore aspect ratio are estimated from the density data, sonic compressional headwave data, and sonic flexural wave data. At block 1407, all the formation properties from the previous block are refined simultaneously from some or all the data. At post-processing block 1408, intervals are flagged where the output from the inversion is biased due to ignoring two-dimensional variation of formation properties.

In each block 1404 to 1407, the relevant properties are estimated by minimizing a cost-function defined as the sum of the data mismatch, where the mismatch is the squared L-2 norm error between the measured and simulated data. A smoothness regularization term is added to the cost-function to reduce non-uniqueness. The minimization algorithm is Gauss-Newton with line-search, box constraints, and adaptive choice of regularization parameter.

The inversion workflow is demonstrated on two examples with noisy simulated data. In a first example, the formation is 100% quartz, containing gas and drilled with oil-based mud. The various fixed parameters for the formation are in Tables 3 and 4 below. These parameters are relevant to a gas-bearing sandstone formation.

TABLE 3

| Component | Bulk Modulus | Shear Modulus | Density |
|---|---|---|---|
| Quartz | 37.0 GPa | 44.0 GPa | 2.65 g/cc |
| Water | 2.74 GPa | — | 1.05 g/cc |
| Oil | 2.04 GPa | — | 0.75 g/cc |
| Gas | 0.02 GPa | — | 0.2 g/cc |

TABLE 4

| Parameter | Value |
|---|---|
| Tortuosity constant, a | 1.0 |
| Cementation exp., m | 1.8 |
| Saturation exp., n | 1.9 |
| Connate water, $R_w$ | 0.11 ohm · m |
| Borehole diameter | 12.25 in. |
| Mud slowness | 265 μsec/ft |
| Mud density | 1.00 g/cc |

Figure 15:
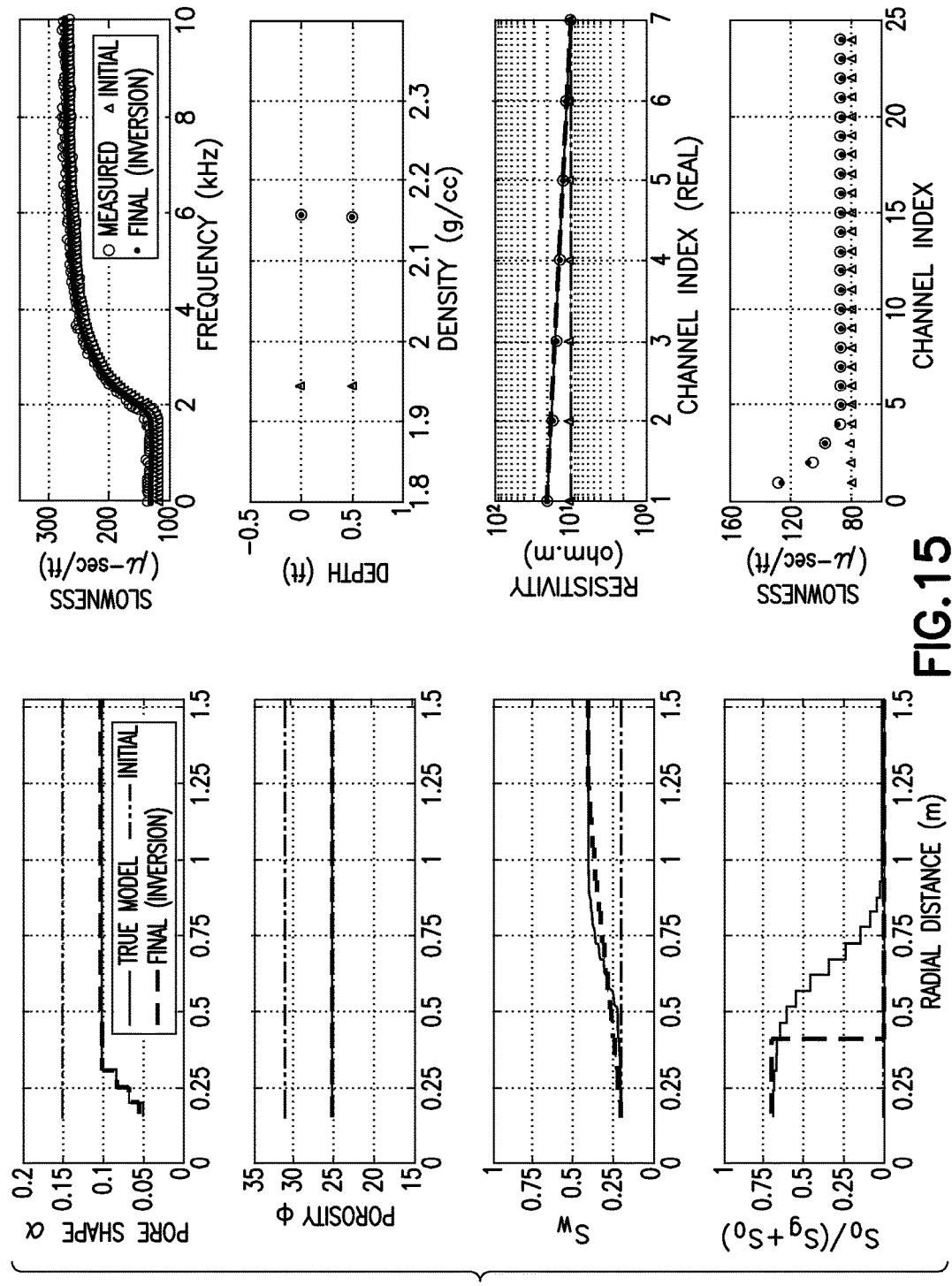
FIG. 15 includes six plots that show inversion results integrating sonic, resistivity, and density data, and solving for the pore aspect ratio and radial profiles in the inversion, in accordance with one embodiment of the present disclosure.

Also, in the first example, the true formation model has constant porosity of 25 pu. The far-field pore aspect ratio is 0.1, which is locally reduced to 0.05 near the wellbore because of mechanical damage. The damaged zone extends one borehole radius into the formation. The water saturation is reduced near the wellbore because of invasion of oil-base mud filtrate and monotonically increases to the far-field value with a ramp profile. The proportion of oil near the wellbore is increased because of the invasion of mud filtrate, whereas there is no oil in the far-field. Thus, the zone where the native pore fluids have been flushed by the invading mud filtrate (also known as the flushed zone) has all three fluid phases, whereas the far-field has only two phases, water and gas. As seen from FIG. 15, the inversion workflow of FIG. 14 can reconstruct the true radial profiles of pore aspect ratio and water saturation, and the constant porosity of the sample in the first example. The inversion is also able to reconstruct the gas saturation in the flushed zone the radial depth of the flushed zone, and the gas saturation in the far-field. Note that the figure shows the radial profile of $S_w$ and $S_o/(S_o+S_g)$. The separate profiles of gas and oil saturation can be determined those profiles with the constraint that $S_w+S_o+S_g=1$. The formation properties are estimated by joint inversion of the density data, array-induction resistivity data, sonic compressional headwave data, and sonic flexural wave data.

Figure 16:
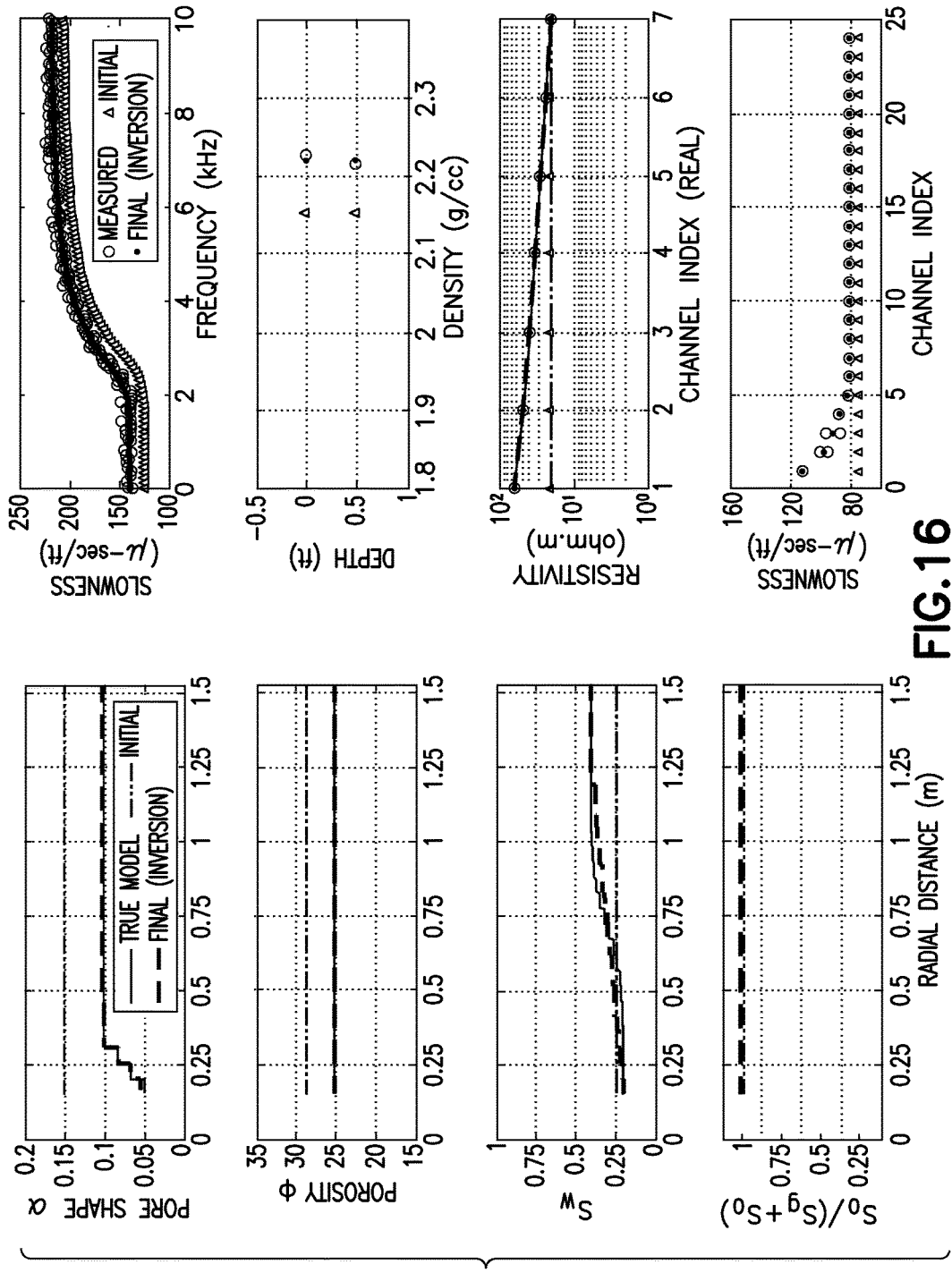
FIG. 16 includes six plots that show inversion results integrating sonic, resistivity, and density data, and solving for the pore aspect ratio and radial profiles in the inversion, in accordance with one embodiment of the present disclosure.

In a second example, the formation is 75% calcite and 25% quartz, containing oil and drilled with oil-base mud. The various fixed parameters are as for the earlier examples for the oil-bearing carbonate formation. In this second example, the formation has only two fluid phases, namely oil and water. This implies that the gas saturation $S_g$ is zero, and hence that $S_o/(S_o+S_g)=1$. However, the difference from the earlier examples is that the porosity is constant and the mechanical damage is characterized by radial variation in pore aspect ratio. As seen from FIG. 16, the inversion workflow can reconstruct the true radial profile of water saturation, radial profile of pore aspect ratio, constant porosity, and constant zero gas saturation for the second example.

Figure 17:
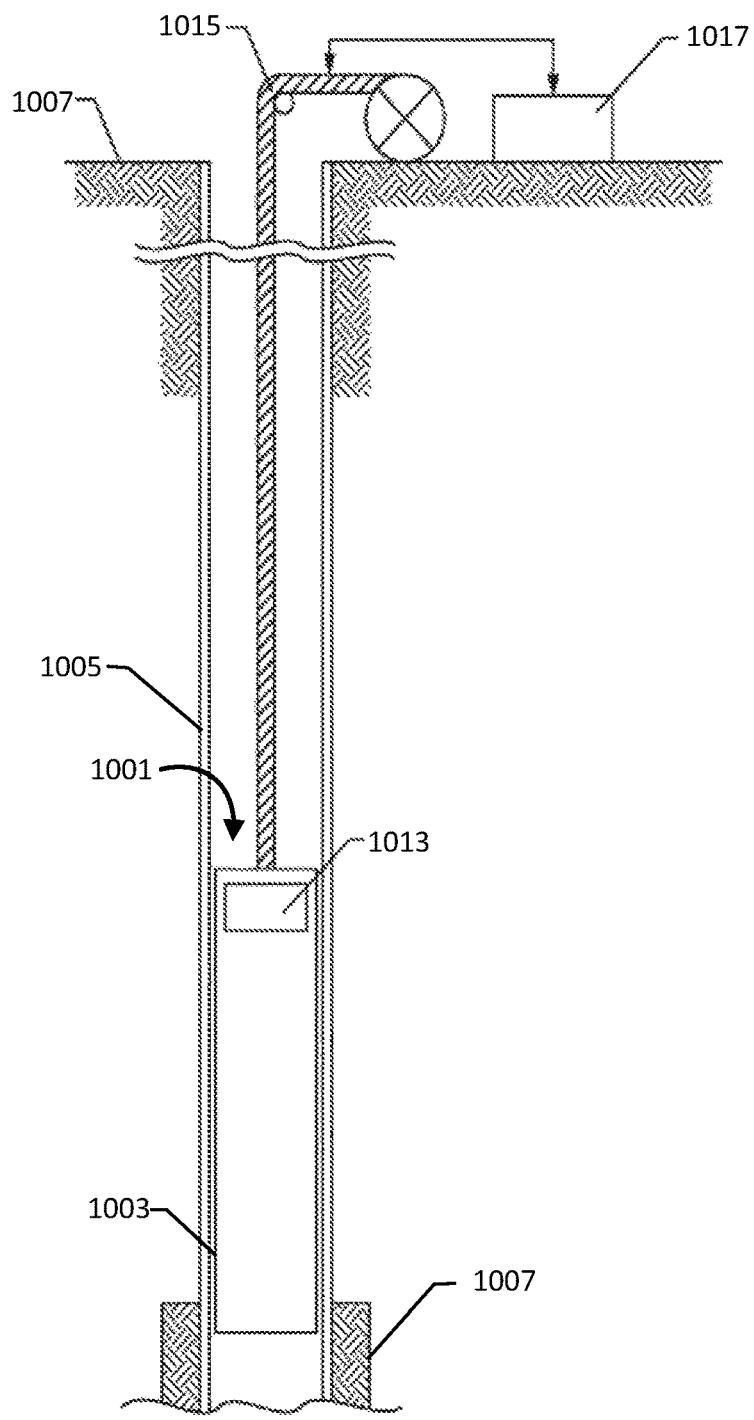
FIG. 17 illustrates an example downhole well logging system that is suitable for carrying out the workflow of FIGS. 1A, 1B, 1C, 2, 3, and/or 14.

FIG. 17 shows an example well logging system that is suitable for carrying out the workflow of FIGS. 1A, 1B, 1C, 2, 3, and/or 14. The system includes one or more downhole well logging instruments 1001 (one shown) with one or more housings 1003 (one shown) shaped and sealed to be moved along the interior of a well or wellbore 1005 that traverses a geological formation 1007. The system in FIG. 17 is a wireline system with a wireline tool. The housing(s) 1003 may contain measurement components for measuring resistivity data, sonic data (such as compression velocity and shear velocity) and density data of the geological formation 1007 as a function of radial direction at an interval of interest in the well or wellbore 1005 as is well known in the art.

By way of example, the measurement components contained with the housing(s) 1003 can include a monopole and dipole sonic logging module that measures sonic data that is sensitive to formation elastic properties at multiple radial depths of investigation (DOI) at an interval of interest within the well or wellbore 1005, with lower frequencies probing deeper into the geological formation 1007 than higher frequencies. The radial DOI of the sonic data measurement into the geological formation 1007 ranges from one-half of the well/wellbore diameter to three times the well/wellbore diameter. The vertical resolution of the sonic data measurement depends on the aperture of the receiver array, which ranges from six feet for the entire array, to one foot with sub-array, multi-shot processing.

The measurement components contained with the housing(s) 1003 can also include a triaxial array induction module that measures resistivity data that is sensitive to formation resistivity at multiple radial depths of investigation at an interval of interest within the wellbore 1005. High frequency and short spacing measurements probe shallower radially into the geological formation 1007 than low frequency and long spacing measurements. The radial DOI of the resistivity data measurement ranges from ten inches to ninety inches into the geological formation 1007. The vertical resolution of the resistivity data measurements ranges from one foot to four feet, with long spacing measurements having lower vertical resolution than short-spacing measurements.

The measurement components contained with the housing(s) 1003 can also include a gamma-gamma density module that measures density data that is sensitive to formation density at multiple radial depths of investigation at an interval of interest within the well or wellbore 1005. The radial DOI of the density data measurements ranges from one inch to three inches into the geological formation 1007. The vertical resolution of the density data measurements ranges from two inches to sixteen inches.

The housing(s) 1003 may also include acquisition and processing electronics 1013 that control the operation of the measurement components, storing data produced by the measurement components, processing the data and storing the results, and couple any desired portion of the data to telemetry components for transmission to the surface. The data may also be stored in the housing(s) 1003 and retrieved at the surface upon removal of the housing(s) 1003 from the well or wellbore 1005.

The housing(s) 1003 may be coupled to an armored electrical cable 1015 that may be extended into and retracted from the well or wellbore 1005. The well or wellbore 1005 may or may not include metal pipe or casing therein. The cable 1015 conducts electrical power to operate the electrical components of the instrument(s) 1001. The cable 1015 can also carry electrical signals between the acquisition and processing electronics 1013 of the instrument(s) 2001 and a surface-located data processing system 1017. In alternate embodiments, coiled tubing or other conveyance mechanism can be used in place of the cable 1015 to convey the instrument(s) 1001 within the wellbore 1005.

Note that data processing operations of FIGS. 1A, 1B, 1C, 2, 3, and/or 14 can be carried out by the acquisition and processing electronics 1013 disposed within the housing(s) 1003, by the surface-located data processing system 1017, or by a combination of the acquisition and processing electronics 1013 and the surface-located data processing system 1017. The acquisition and processing electronics 1013 and/or the data processing system 1017 may include one or more digital-signal processors, one or more general purpose processors, and/or one or more computer or computer systems as will be explained below with reference to FIG. 18 for analysis of the acquired data as well as devices for recording the acquired data with respect to position in the wellbore and/or time.

Figure 18:
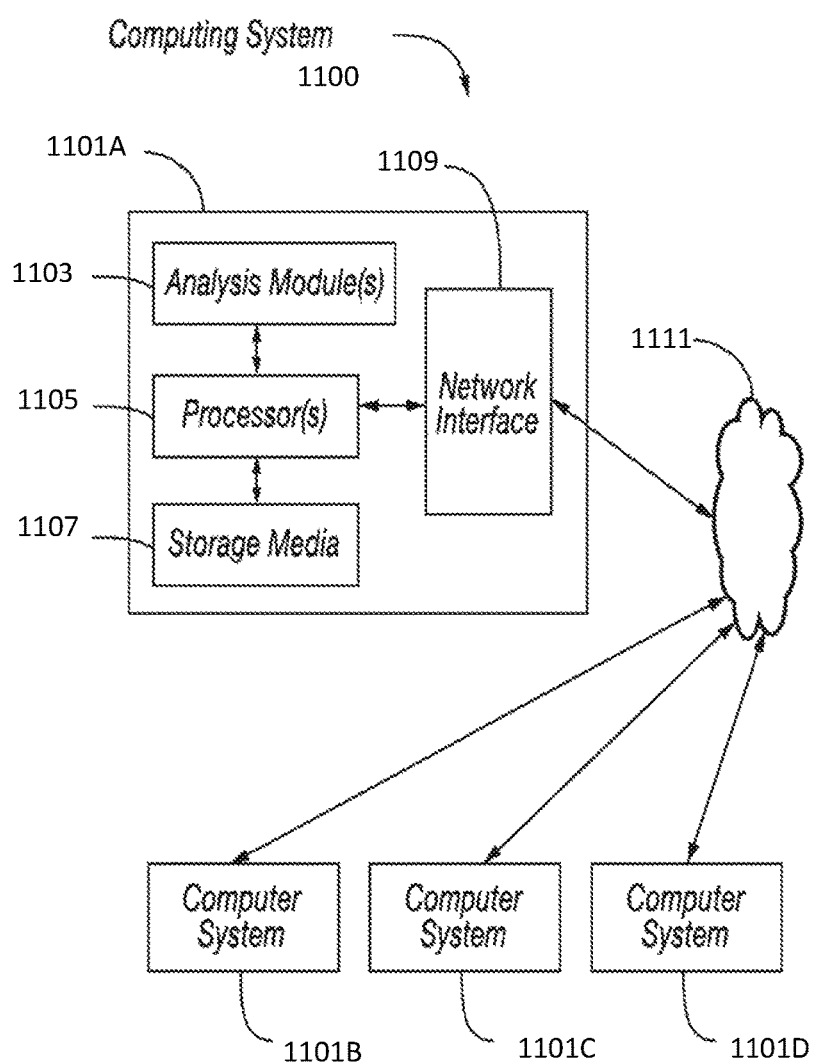
FIG. 18 illustrates an example computing system in accordance with some embodiments for carrying out the example workflow such as those to be explained above with reference to FIGS. 1A, 1B, 1C, 2, 3, and/or 14.

FIG. 18 shows an example computing system 1100 in accordance with some embodiments for carrying out the example workflow such as those to be explained above with reference to FIGS. 1A, 1B, 1C, 2, 3, and/or 14. The computing system 1100 can be an individual computer system 1101A or an arrangement of distributed computer systems. The computer system 1101A includes one or more analysis modules 1103 (a program of computer-executable instructions and associated data) that can be configured to perform various tasks according to some embodiments, such as the tasks described above. To perform these various tasks, an analysis module 1103 executes on one or more processors 1105, which is (or are) connected to one or more storage media 1107. The processor(s) 1105 can also be connected to a network interface 1109 to allow the computer system 1101A to communicate over a data network 1111 with one or more additional computer systems and/or computing systems, such as 1101B, 1101C, and/or 1101D. Note that computer systems 1101B, 1101C and/or 1101D may or may not share the same architecture as computer system 1101A, and may be located in different physical locations, e.g. computer systems 1101A and 1101B may be on a drilling rig on the ocean or in a well logging unit disposed proximate a wellbore drilling operation, while in communication with one or more computer systems such as 1101C and/or 1101D that are located in one or more data centers on shore, other ships, and/or located in varying countries on different continents. Any one or more of the computer systems may be disposed in the well logging instrument (whether wireline as in FIG. 17 or LWD as in FIG. 19).

The processor 1105 can include a microprocessor, microcontroller, processor module or subsystem, programmable integrated circuit, programmable gate array, digital signal processor (DSP), or another control or computing device.

The storage media 1107 can be implemented as one or more non-transitory computer-readable or machine-readable storage media. Note that while in the embodiment of FIG. 18, the storage media 1107 is depicted as within computer system 1101A, in some embodiments, storage media 1107 may be distributed within and/or across multiple internal and/or external enclosures of computing system 1101A and/or additional computing systems. Storage media 1107 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the computer-executable instructions and associated data of the analysis module(s) 1103 can be provided on one computer-readable or machine-readable storage medium of the storage media 1107, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 1100 is only one example of a computing system, and that computing system 1100 may have more or fewer components than shown, may combine additional components not depicted in the embodiment of FIG. 18, and/or computing system 1100 may have a different configuration or arrangement of the components depicted in FIG. 18. The various components shown in FIG. 18 may be implemented in hardware, software, or a combination of both hardware and software, including one or more signal processing and/or application specific integrated circuits.

Further, the operations of the workflow described above may be implemented by running one or more functional modules in information processing apparatus such as general purpose processors or application specific chips, such as ASICs, FPGAs, PLDs, SOCs, or other appropriate devices. These modules, combinations of these modules, and/or their combination with general hardware are all included within the scope of protection.

Figure 19:
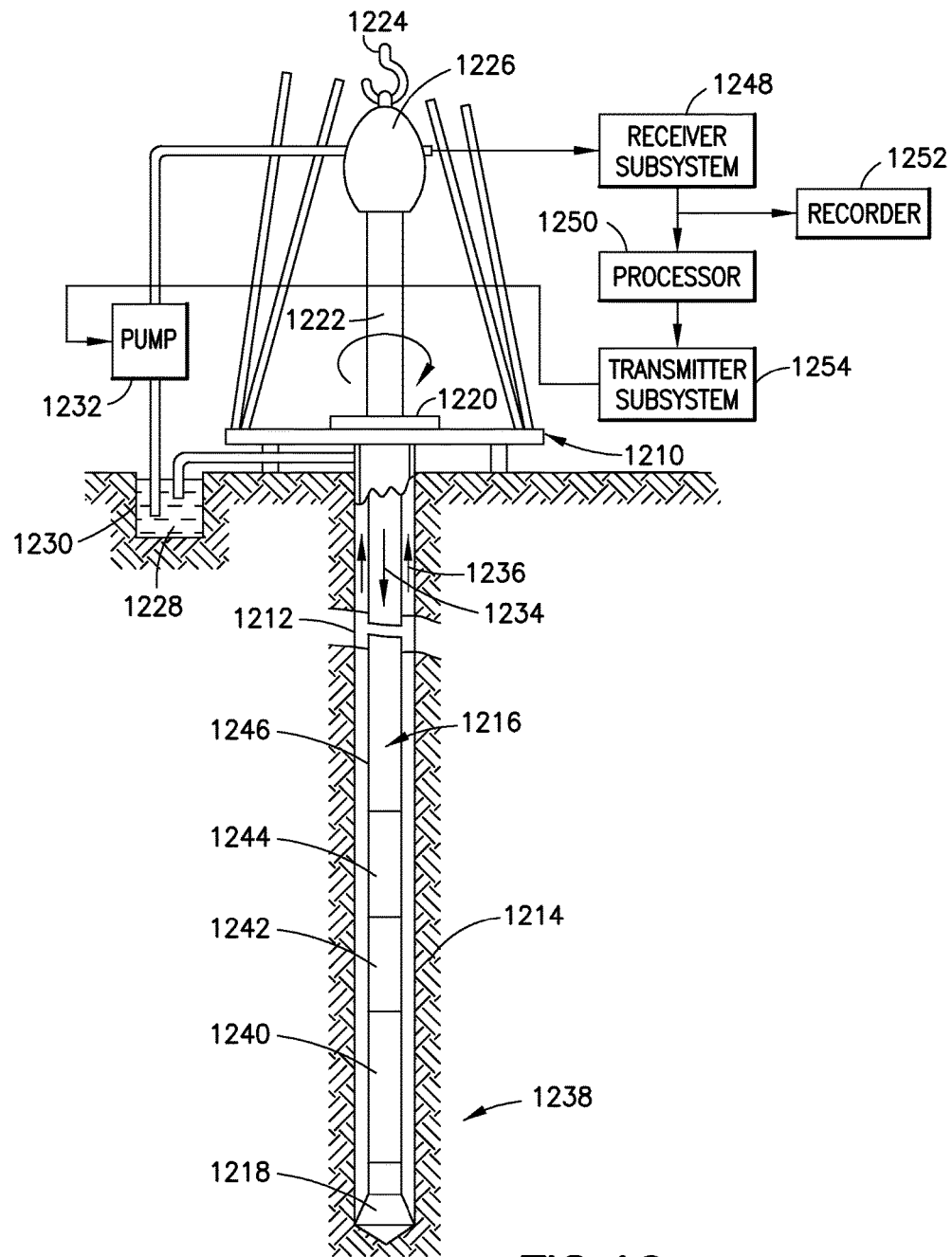
FIG. 19 illustrates an example logging-while-drilling (LWD) system that is suitable for carrying out the workflow of FIGS. 1A, 1B, 1C, 2, 3, and/or 14.

FIG. 19 shows an example logging-while-drilling (LWD) system that is suitable for carrying out the workflow of FIGS. 1A, 1B, 1C, 2, 3, and/or 14. In this system, a platform and derrick 1210 are positioned over a wellbore 1212 that may be formed in the geological formation 1214 by rotary drilling. A drill string 1216 may be suspended within the wellbore 1212 and may include a drill bit 1218 attached thereto and rotated by a rotary table 1220 (energized by means not shown), which engages a kelly 1222 at the upper end of the drill string 1216. The drill string 1216 is typically suspended from a hook 1224 attached to a traveling block (not shown). The kelly 1222 may be connected to the hook 1224 through a rotary swivel 1226 which permits rotation of the drill string 1216 relative to the hook 1224. Alternatively, the drill string 1216 and drill bit 1218 may be rotated from the surface by a "top drive" type of drilling rig.

Drilling fluid or mud 1228 is contained in a mud pit 1230 adjacent to the derrick 1210. A pump 1232 pumps the drilling fluid 1228 into the drill string 1216 via a port in the swivel 1226 to flow downward (as indicated by the flow arrow 1234) through the center of the drill string 1216. The drilling fluid exits the drill string via ports in the drill bit 1218 and then circulates upward in the annular space between the outside of the drill string 1216 and the wall of the wellbore 1212, as indicated by the flow arrows 1236. The drilling fluid 1228 thereby lubricates the drill bit 1218 and carries formation cuttings to the surface. At the surface, the drilling fluid 1228 is returned to the mud pit 1230 for recirculation. If desired, a directional drilling assembly (not shown) could also be employed.

A bottom hole assembly ("BHA") 1238 may be mounted within the drill string 1216, preferably near the drill bit 1218. The BHA 1238 may include subassemblies for making measurements, processing and storing information and for communicating with surface-located components. Such measurements may correspond to those made using the instrument 1001 as explained above with reference to FIG. 17. The BHA 1238 is typically located within several drill collar lengths of the drill bit 1218. In the illustrated BHA 1238, a stabilizer collar section 1240 is shown disposed immediately above the drill bit 1218, followed in the upward direction by a drill collar section 1242, another stabilizer collar section 1244 and another drill collar section 1246. This arrangement of drill collar sections and stabilizer collar sections is illustrative only, and other arrangements of components in any implementation of the BHA 1238 may be used. The need for or desirability of the stabilizer collars will depend on drilling conditions as well as on the demands of the measurement.

In the arrangement shown in FIG. 19, the measurement components of the well logging instrument may be located in the drill collar section 1242 above the stabilizer collar 1240. Such components could, if desired, be located closer to or farther from the drill bit 1218, such as, for example, in either stabilizer collar section 1240 or 1244 or the drill collar section 1246.

The BHA 1238 may also include a telemetry subassembly (not shown) for data and control communication with surface-located components. Such telemetry subassembly may be of any suitable type, e.g., a mud pulse (pressure or acoustic) telemetry system, wired drill pipe, etc., which receives output signals from LWD measuring instruments in the BHA 1238) and transmits encoded signals representative of such outputs to the surface where the signals are received and decoded in a receiver subsystem 1248, and supplied to a processor 1250 and/or a recorder 1252. A surface transmitter subsystem 1254 may also be provided for establishing communication with the BHA 1238.

Power for the LWD instrumentation of the BHA 1238 may be provided by battery or, as known in the art, by a turbine generator disposed in the BHA 1238 and powered by the flow of drilling fluid. The LWD instrumentation may also include directional sensors (not shown separately) that make measurements of the geomagnetic orientation or geodetic orientation of the BHA 1238 and the gravitational orientation of the BHA 1238, both rotationally and axially.

Note that data processing operations of FIGS. 1A, 1B, 1C, 2, 3, and/or 14 can be carried out by the acquisition and processing electronics of the BHA 1238, by the surface-located data processor 1250, or by a combination of the acquisition and processing electronics of the BHA 1238 and the surface-located processor 1250. The acquisition and processing electronics of the BHA 1238 and/or the processor 1250 may include a one or more digital-signal processors, one or more general purpose processors, and/or one or more computer or computer systems as discussed above with reference to FIG. 18 for analysis of the detected signals as well as devices for recording the signals communicated from the BHA 1238 with respect to position in the wellbore and/or time.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:

1. A method for determining properties of a formation traversed by a well or wellbore, the method comprising:
   on a data processing system, obtaining measured sonic data, resistivity data, and formation density data for an interval-of-interest within the well or wellbore;
   on the data processing system, deriving a formation model that describes properties of the formation at the interval-of-interest, wherein the formation model is based on the measured sonic data, resistivity data, and formation density data for the interval-of-interest;
   on the data processing system, using the formation model as input to a plurality of petrophysical transforms and corresponding tool response simulators that derive simulated sonic data, resistivity data, and formation density data for the interval-of-interest; and
   on the data processing system, using the measured sonic data, resistivity data, and formation density data for the interval-of-interest and the simulated sonic data, resistivity data, and formation density data for the interval-of-interest to refine the formation model and determine properties of the formation at the interval-of-interest.

2. The method of claim 1, wherein:
   the properties of the formation comprise at least one of the following properties: (i) a radial porosity profile, (ii) a radial water saturation profile, (iii) a pore aspect ratio, (iv) a porosity, (v) a radial gas saturation profile, (vi) a radial oil saturation profile, and (vii) a radial profile of pore aspect ratio.

3. The method of claim 2, further comprising:
   on the data processing system, determining the pore aspect ratio of the formation model for the interval-of-interest based on the measured sonic data and formation density data for the interval-of-interest as well as the simulated sonic data and formation density data for the interval-of-interest.

4. The method of claim 2, further comprising:
   on the data processing system, determining the radial porosity profile of the formation model for the interval-of-interest based on the measured sonic data and formation density data for the interval-of-interest as well as the simulated sonic data and formation density data for the interval-of-interest.

5. The method of claim 2, further comprising:
on the data processing system, determining both the pore aspect ratio and the radial porosity profile of the formation model for the interval-of-interest by minimizing a cost-function defined as a weighted sum of a sonic data mismatch between the measured and simulated sonic data for the interval-of-interest and a weighted sum of a formation density data mismatch between the measured and simulated formation density data for the interval-of-interest.

6. The method of claim 2, further comprising:
on the data processing system, determining the radial water saturation profile of the formation model for the interval-of-interest based on the measured and simulated resistivity data for the interval-of-interest.

7. The method of claim 2, further comprising:
using the pore aspect ratio of the formation model to determine whether the interval-of-interest includes a particular porosity type belonging to certain porosity types, which include one porosity type that includes micropores and another porosity type that includes macropores.

8. The method of claim 2, further comprising:
(i) on the data processing system, determining an initial radially-constant pore aspect ratio, porosity, water saturation, gas saturation, and oil saturation of the formation model for the interval-of-interest based on the measured sonic data and formation density data for the interval-of-interest as well as the simulated sonic data and formation density data for the interval-of-interest;
(ii) on the data processing system, determining an initial radial water saturation profile of the formation model based on the measured and simulated sonic data and the initial radially constant pore aspect ratio, porosity, oil saturation, and gas saturation of the formation model;
(iii) on the data processing system, determining an intermediate porosity, an initial radial profile of gas saturation, an initial radial profile of oil saturation, and an initial radial profile of pore aspect ratio of the formation model based on the measured and simulated formation density data, sonic compressional headwave data, and sonic flexural wave data; and
(iv) on the data processing system, simultaneously determining a final porosity, and final profiles of water saturation, gas saturation, oil saturation, and pore aspect ratio of the formation model based on the measured sonic and formation density data for the interval-of-interest, the simulated sonic and formation density data for the interval-of-interest, sonic compressional headwave data, sonic flexural wave data, as well as the intermediate porosity, the initial radial profile of gas saturation, the initial radial profile of oil saturation, and the initial radial profile of pore aspect ratio determined in (iii).

9. The method of claim 1, further comprising:
on the data processing system, using a first petrophysical transform to derive a radial profile of resistivity for the interval-of-interest based on the formation model for the interval-of-interest; and
on the data processing system, using a first tool response simulator to derive the simulated resistivity data for the interval-of-interest based on the radial profile of resistivity for the interval-of-interest.

10. The method of claim 9, wherein:
the first petrophysical transform is based on Archie's Law.

11. The method of claim 1, further comprising:
on the data processing system, using a second petrophysical transform to derive a radial profile of compressional wave velocity and shear wave velocity for the interval-of-interest based on the formation model for the interval-of-interest; and
on the data processing system, using a second tool response simulator to derive the simulated sonic data for the interval-of-interest based on the radial profile of compressional wave velocity and shear wave velocity as well as pore aspect ratio for the interval-of-interest.

12. The method of claim 11, wherein:
the second petrophysical transform is based on a rock physics model.

13. The method of claim 1, further comprising:
on the data processing system, using a third petrophysical transform to derive a radial profile of formation density for the interval-of-interest based on the formation model for the interval-of-interest; and
on the data processing system, using a third tool response simulator to derive the simulated formation density data for the interval-of-interest based on the radial profile of formation density for the interval-of-interest.

14. The method of claim 13, wherein:
the third petrophysical transform is based on a density mixing law.

15. The method of claim 1, wherein:
the formation model comprises a one-dimensional radial formation model.

16. The method of claim 1, further comprising:
using at least one downhole tool to obtain the measured sonic data, resistivity data, and formation density data for the interval-of-interest.

17. The method of claim 16, wherein:
the at least one downhole tool is one of the following downhole tools: a wireline tool and a logging-while-drilling tool.

18. A non-transitory computer readable storage medium storing a program executed on a data processing system for executing a method that determines properties of a formation traversed by a well or wellbore, the method comprising:
on the data processing system, obtaining measured sonic data, resistivity data, and formation density data for an interval-of-interest within the well or wellbore;
on the data processing system, deriving a formation model that describes properties of the formation at the interval-of-interest, wherein the formation model is based on the measured sonic data, resistivity data, and formation density data for the interval-of-interest;
on the data processing system, using the formation model as input to a plurality of petrophysical transforms and corresponding tool response simulators that derive simulated sonic data, resistivity data, and formation density data for the interval-of-interest; and
on the data processing system, using the measured sonic data, resistivity data, and formation density data for the interval-of-interest and the simulated sonic data, resistivity data, and formation density data for the interval-of-interest to refine the formation model and determine properties of the formation at the interval-of-interest.

19. The non-transitory computer readable storage medium of claim 18, wherein:
the properties of the formation comprise at least one of the following properties: (i) a radial porosity profile, (ii) a radial water saturation profile, (iii) a pore aspect ratio, (iv) a porosity, (v) a radial gas saturation profile, (vi) a radial oil saturation profile, and (vii) a radial profile of pore aspect ratio.

20. The non-transitory computer readable storage medium of claim 19, wherein the method further comprises:
   on the data processing system, using the measured sonic data and formation density data for the interval-of-interest as well as the simulated sonic data and formation density data for the interval-of-interest to calculate the pore aspect ratio of the formation model for the interval-of-interest.

21. The non-transitory computer readable storage medium of claim 19, wherein the method further comprises:
   on the data processing system, using the measured sonic data and formation density data for the interval-of-interest as well as the simulated sonic data and formation density data for the interval-of-interest to calculate the radial porosity profile of the formation model for the interval-of-interest.

22. The non-transitory computer readable storage medium of claim 19, wherein the method further comprises:
   on the data processing system, calculating both the pore aspect ratio and the radial porosity profile of the formation model for the interval-of-interest by minimizing a cost-function defined as a weighted sum of a sonic data mismatch between the measured and simulated sonic data for the interval-of-interest and a weighted sum of a formation density data mismatch between the measured and simulated formation density data for the interval-of-interest.

23. The non-transitory computer readable storage medium of claim 19, wherein the method further comprises:
   on the data processing system, using the measured and simulated resistivity data for the interval-of-interest to calculate the radial water saturation profile of the formation model for the interval-of-interest.

* * * * *